US008420617B2

(12) United States Patent
Tkachuk

(10) Patent No.: US 8,420,617 B2
(45) Date of Patent: Apr. 16, 2013

(54) MULTIANTIVIRUS COMPOUND, COMPOSITION AND METHOD FOR TREATMENT OF VIRUS DISEASES

(75) Inventor: Zenoviy Tkachuk, Kiev (UA)

(73) Assignee: Biocell Laboratories, Washington, DC (US)

( * ) Notice: Subject to any disclaimer, the term of this patent is extended or adjusted under 35 U.S.C. 154(b) by 122 days.

(21) Appl. No.: 13/046,240

(22) Filed: Mar. 11, 2011

(65) Prior Publication Data

US 2012/0232129 A1    Sep. 13, 2012

(51) Int. Cl.
| | |
|---|---|
| A61K 31/70 | (2006.01) |
| C07H 21/02 | (2006.01) |
| C07H 21/04 | (2006.01) |
| C12Q 1/68 | (2006.01) |

(52) U.S. Cl.
USPC ...... 514/44 A; 514/44 R; 536/23.1; 536/24.1; 536/24.5

(58) Field of Classification Search .................. None
See application file for complete search history.

(56) References Cited

U.S. PATENT DOCUMENTS

| | | | |
|---|---|---|---|
| 3,615,654 | A | 10/1971 | Ayukawa et al. |
| 3,914,450 | A | 10/1975 | Robbins et al. |
| 5,712,256 | A | 1/1998 | Kulkarni et al. |
| 6,291,637 | B1 | 9/2001 | Das et al. |
| 6,737,271 | B1 | 5/2004 | Tkachuk |
| 7,153,839 | B2 | 12/2006 | Tkachuk |
| 7,683,036 | B2 | 3/2010 | Esau et al. |
| 7,759,319 | B2 | 7/2010 | Lollo et al. |
| 2009/0203893 | A1 | 8/2009 | Esau et al. |
| 2009/0236225 | A1 | 9/2009 | Esau et al. |
| 2009/0286969 | A1 | 11/2009 | Esau et al. |
| 2009/0291906 | A1 | 11/2009 | Esau et al. |
| 2009/0291907 | A1 | 11/2009 | Esau et al. |
| 2009/0292005 | A1 | 11/2009 | Ohgi et al. |
| 2009/0298174 | A1 | 12/2009 | Esau et al. |
| 2009/0317907 | A1 | 12/2009 | Esau et al. |
| 2010/0124557 | A1 | 5/2010 | Oberreither et al. |
| 2010/0249215 | A1 | 9/2010 | Lollo et al. |
| 2010/0267813 | A1 | 10/2010 | Esau et al. |
| 2010/0267814 | A1 | 10/2010 | Bennett et al. |

FOREIGN PATENT DOCUMENTS

| | | |
|---|---|---|
| EP | 2003140 A2 | 12/2008 |
| RU | 2268067 C2 | 1/2006 |
| WO | 94/02595 A1 | 2/1994 |
| WO | 2008-106979 A2 | 9/2008 |
| WO | 2010-056991 A1 | 5/2010 |

OTHER PUBLICATIONS

Invitation to Pay Additional Fees and, Where Applicable, Protest Fee (PCT Article 17(3)(a) and Rule 40.1 and 40.1 and 40.2(e)) date of mailing May 3, 2012, issued in corresponding International Application No. PCT/US2012/027460, (9 pages).
Database WPI Week 200632 Thomson Scientific, London, GB; AN 2006-303028 XP002674405, & RU 2268067 C2 (Immunology Inst) Jan. 20, 2006.1page. Cited in Form PCT/ISA/206 dated May 3, 2012 in corresponding PCT/US2012/027460.

Arbuthnot, Patrick; "Harnessing rna interference for the treatment of viral infections"; Drug News and Perspectives, PROUS Science, vol. 23, No. 6, Jul. 1, 2010, pp. 341-350, XP001537436. Cited in Form PCT/ISA/206 dated May 3, 2012 in corresponding PCT/US2012/027460.
Anonymous; "Sodium nucleinate (Nucleinate Sodium)", Russian Drug Compendium Vidal, Jan. 1, 2005, pp. 1-7, XP007920527, Retrieved from the Internet: URL:http://www.vidal.ru/poisk_preparatov/nucleinate-sodium.htm. Cited in Form PCT/ISA/206 dated May 3, 2012 in corresponding PCT/US2012/027460.
Dykxhoorn, Derek M. et al.; "Silencing Viral Infection"; PLOS Medicine, vol. 3, No. 7, Jan. 1, 2006, pp. 1000-1004 (E242), XP55024955. Cited in Form PCT/ISA/206 dated May 3, 2012 in corresponding PCT/US2012/027460.
Frolov V M et al., "[Use of Sodium nucleinate in the overall therapy of viral hepatitis in children]", Voprosy Ochrany Materinstva I Detstva: E Emesjaenyj Naueno-Praktieeskij Urnal, Moskva: Medicina, RU, vol. 25, No. 9, Sep. 1, 1980, pp. 12-15, XP008151063. Cited in Form PCT/ISA/206 dated May 3, 2012 in corresponding PCT/US2012/027460.
Tkachuk, Z.Y. et al., "Anti-influenzal activity of Nuclex medicine," Reports of the National Academy of Sciences of Ukraine, 2010, No. 9, pp. 191-196.
Porva, Y.I. et al., "Antivirus Activity of Nuclex on the Cellular Model of Hepatitis C Virus," Pharmacology and pharmaceutics reporter, Oct. 2010, No. 7-8, pp. 10-16.
Tkachuk, Z. et al., "Specific antiviral drug Nuclex action in cardiovascular disorders, influenza and SARS," Problems of ecological and medical genetics and clinical immunology, Scientific Papers, 2010, No. 4, pp. 312-333.
International Searh Report of counterpart PCT/US2012/027460, dated Aug. 20, 2012.
Tkachuk, Z.Y. et al., "Anti-influenzal activity of Nuclex medicine," Reports of the National Academy of Sciences of Ukraine, Sep. 2010, No. 9, pp. 191-196.
Porva, Y.I. et al., "Antivirus Activity of Nuclex on the Cellular Model of Hepatitis C Virus," Pharmacology and pharmaceutics reporter, Sep. 2010, No. 9, pp. 10-16.
Tkachuck, Z.Y. et al., "Specific antiviral drug Nuclex action in cardiovascular disorders, influenza and SARS," Problems of ecological and medical genetics and clinical immunology, Scientific Papers, Dec. 2010, No. 4, pp. 312-333.
Saravolac, E.G. et al., "Recent Patents on Development of Nucleic Acid-Based Antiviral Drugs against Seasonal and Pandemic Influenza Virus Infections," Frontiers in Anti-Infective Drug Discovery, No. 1, pp. 409-425 (2010).
Thompkins, S.M. et al., "Protection against lethal influenza virus challenge by RNA interference in vivo," PNAS, vol. 101, No. 23, pp. 8682-8686 (2004).

*Primary Examiner* — Sean McGarry

(74) *Attorney, Agent, or Firm* — Westerman, Hattori, Daniels & Adrian, LLP

(57) ABSTRACT

A method for obtaining a new antiviral compound with multiple action against many viruses, comprising modified highly purified yeast RNA, a pharmaceutical composition comprising such RNA, and a method for the treatment and prevention of viral disease comprising administering to a patient a composition comprising an amount effective to ameliorate the symptoms of viral disease of ribonucleic acid. The exogenous modified yeast RNA has a pronounced multiple anti-virus action in a wide range of concentrations. The modified yeast RNA is capable of inhibiting the reproduction of viruses from Orthomyxoviridae, Paramyxovirus, Hepatitis, Herpesviridae families, enterovirus and adenovirus. Also, the modified yeast RNA is capable of inhibiting the reproduction of influenza viruses, hepatitis C virus, genital herpes, human immunodeficiency virus and Coxsackie B virus.

27 Claims, 4 Drawing Sheets

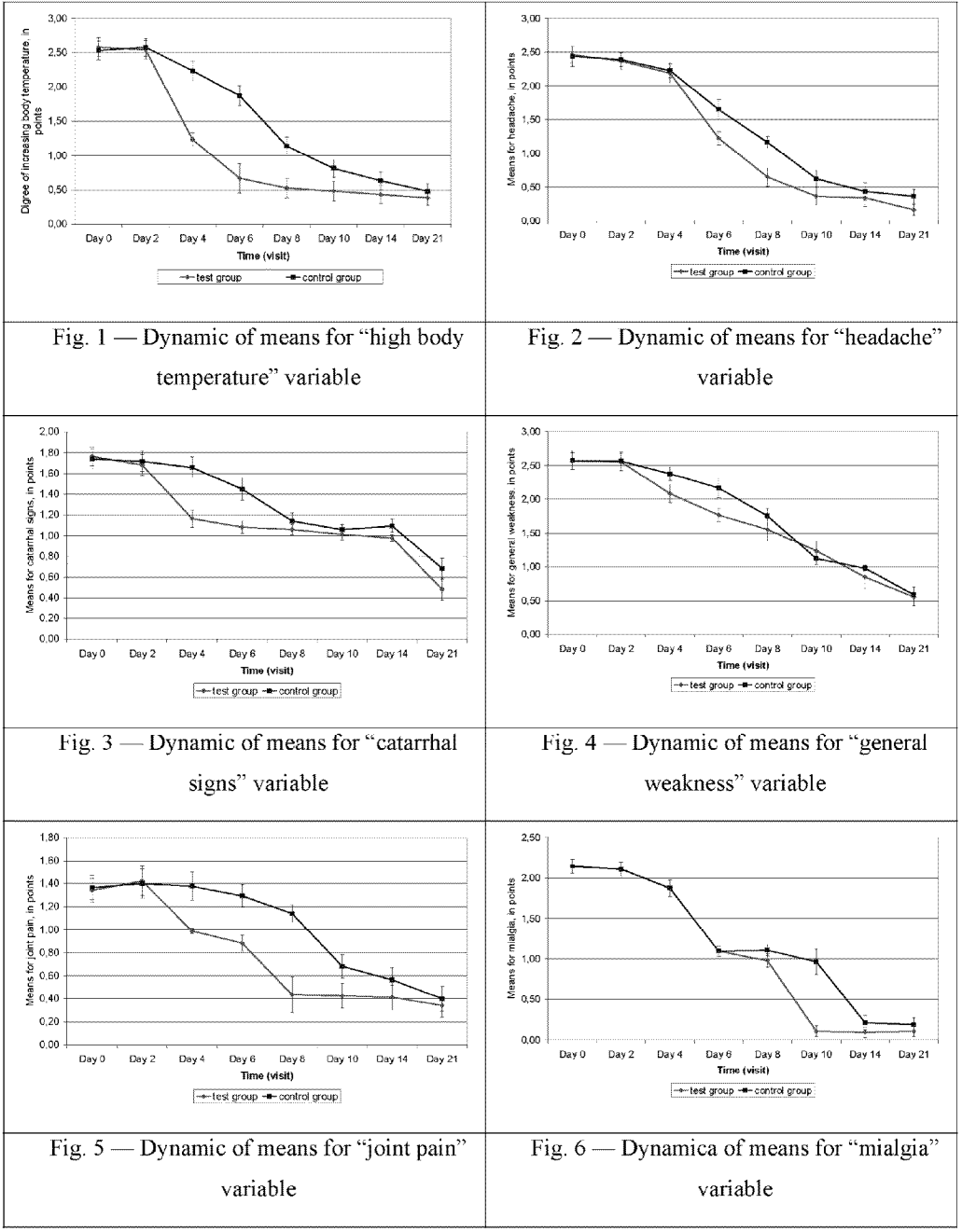

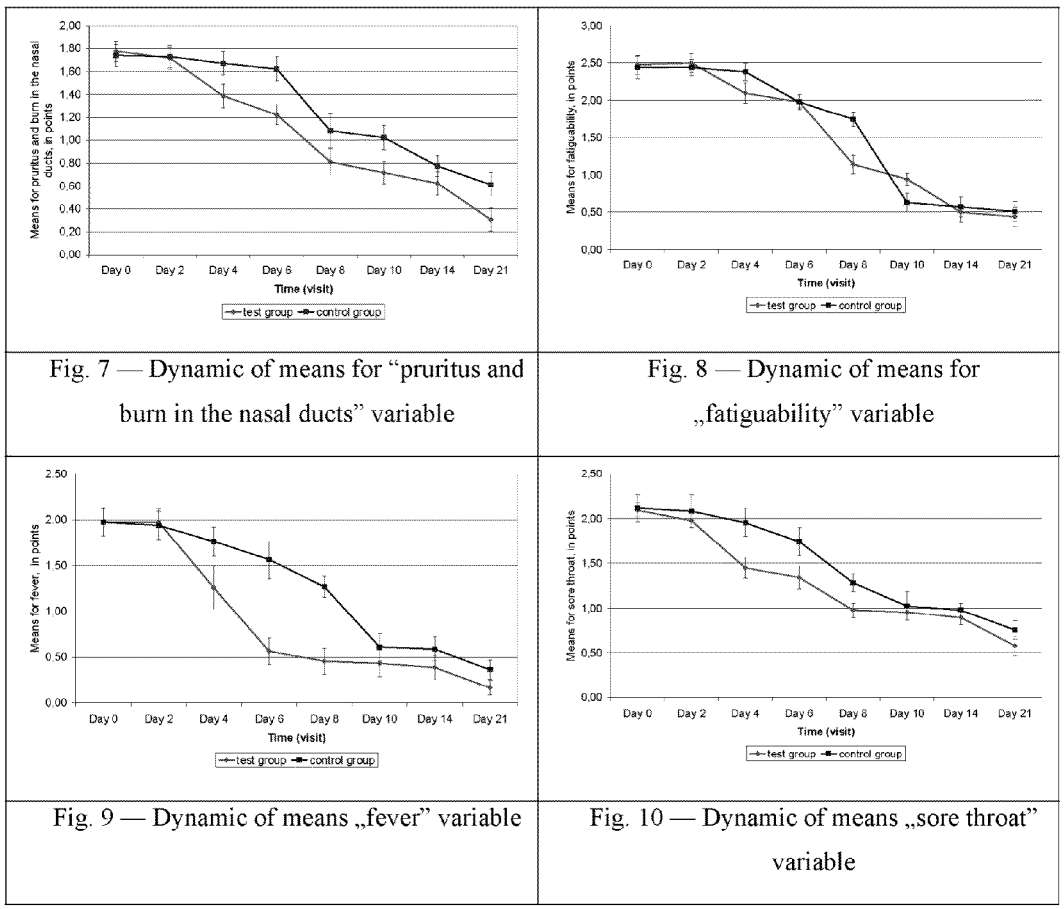

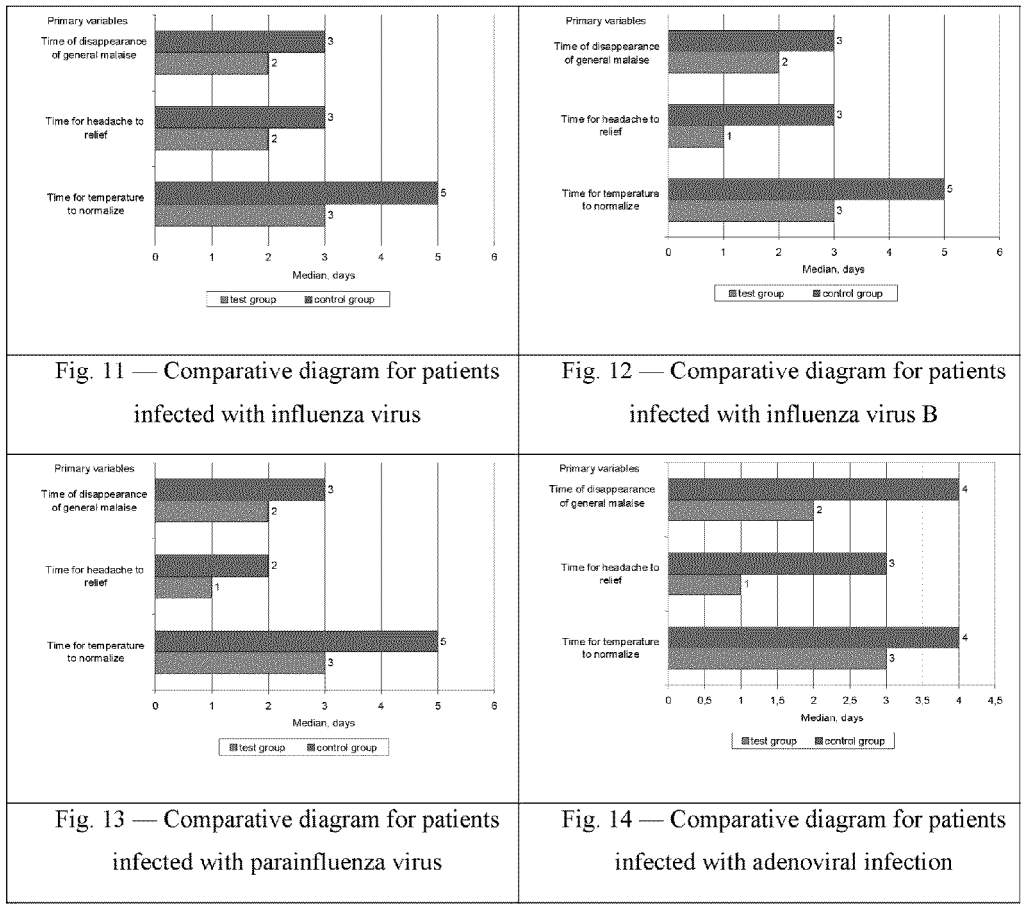
Fig. 11 — Comparative diagram for patients infected with influenza virus
Fig. 12 — Comparative diagram for patients infected with influenza virus B
Fig. 13 — Comparative diagram for patients infected with parainfluenza virus
Fig. 14 — Comparative diagram for patients infected with adenoviral infection

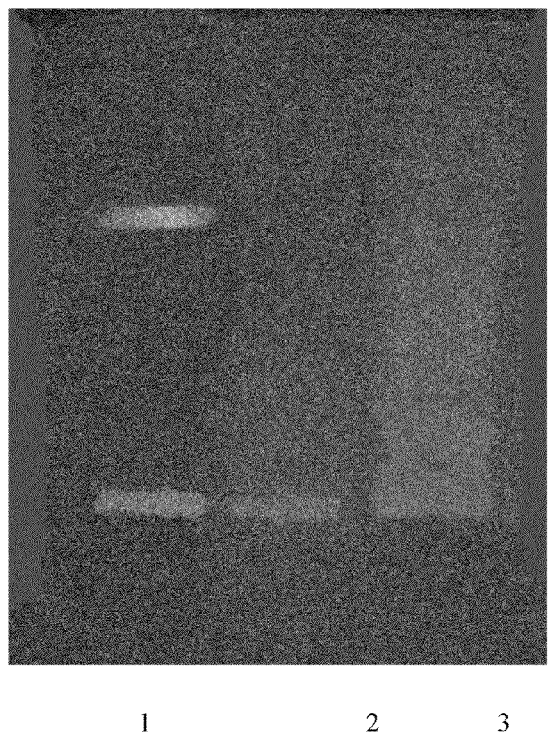
Figure 15. Electrophoresis for small RNA in 15% PAAG, containing DS-Na and 7M urea, drugs: E.Coli тRNA (stripe-1, sector-a), 25-member oligonucleotide (stripe-1, sector-b), highly purified yeast RNA (stripe-2), sodium salt of yeast RNA (stripe-3)

MULTIANTIVIRUS COMPOUND, COMPOSITION AND METHOD FOR TREATMENT OF VIRUS DISEASES

BACKGROUND OF THE INVENTION

The rapidly increasing resistance rate to antiviral agents necessitates new combination drugs with different mechanism of action as well as novel drugs acting on newly discovered targets. As viral diseases are frequently associated with several kinds of viruses, the research on novel antiviral agents with multiple mechanisms of action on as many viruses as possible is of particular importance for the improvement of treatment outcomes.

RNA molecules can adopt a wide variety of conformations and perform a range of cellular functions. This is achieved due to their structure allowing them to form specific RNA-RNA, RNA-DNA or RNA-protein interactions. Achievements in the study of these RNA interactions permitted to develop novel methods of treatment of various disorders. So far the most attention has been received by therapeutic RNAs which can be classified as gene inhibitors, gene amenders, protein inhibitors and immunostimulatory RNAs. (Bruce A. Sullenger & Eli Gilboa, Emerging clinical applications of RNA, Nature, 2002, 418, July 11, pp. 252-258)

Gene inhibitors are represented by complementary RNAs which specifically recognize their target transcripts by forming base pairs with them in a sequence-dependent manner. They are also termed antisense RNAs. The formation of this RNA duplex is believed to lead to the degradation of the target RNA or the inhibition of its translation. Further discovery that certain RNAs can perform catalysis of RNA hydrolysis led the development of a novel class of therapeutic RNAs called trans-cleaving ribozymes. Such ribozymes bind substrate RNAs through base-pairing interactions, cleave the bound target RNA, thus releasing the cleavage products. (Guerrier-Takada, C., Gardiner, K., Marsh, T., Pace, N. & Altman, S, The RNA moiety of ribonuclease P is the catalytic subunit of the enzyme, Cell, 1983, 35, pp. 849-857) Several phase I and phase II trials have been initiated using trans-cleaving ribozymes in a small number of patients with infectious diseases. (Wong-Staal, F., Poeschla, E. M. & Looney, D. J., A controlled, Phase I clinical trial to evaluate the safety and effects in HIV-1 infected humans of autologous lymphocytes transduced with a ribozyme that cleaves HIV-1 RNA, Hum. Gene Ther. 1998, 9, pp. 2407-2425) Unfortunately, as shown in these trials, a sustained long-term effect has not been achieved. (Bruce A. Sullenger & Eli Gilboa, Emerging clinical applications of RNA, Nature, 2002, 418, July 11, pp. 252-258) The critical factors determining the success of these synthetic ribozyme efficacy trials include the ability to deliver ribozymes efficiently into the appropriate cells in vivo, and the level and duration of target-gene inhibition that is required to slow the rate of disease progression. To benefit patients with chronic diseases such as cancer, HIV-infection, and hepatitis C, long-term and high-level inhibition of target transcripts is required. In practice this may be difficult to achieve, especially when targeting highly expressed viral RNAs. Protein inhibitors are represented by artificially-produced RNAs which can adopt complex secondary structures that allow them to bind target proteins with high affinity and specificity. (Daley D. T. A., Luscombe N. M., Berman H. M. and Thornton J. M., Protein-RNA interactions: a structural analysis. Nucleic Acids Research, 29, 4, pp. 943-954) For selection of these biologically active RNAs representing oligonucleotides 15-35 nucleotides long, a number of methods has been developed. Such oligonucleotides can specifically bind target proteins. (A. D. Keefe, S. Pai, A. Ellington, Aptamers as therapeutics, Nature Review, 2010, 9, pp. 537-550)

First of all, technologies of oligonucleotide synthesis have been developed, permitting synthetic ologinucleotides to bind a wide range of target proteins with high affinity. Target proteins include cytokines, proteases, kinases, cell surface receptors and cell adhesion molecules. Currently synthetic oligonucleotides are being developed which can be administered systemically into organism and bind blood targets (such as thrombin, IXa factor, von Willebrand factor) or cell surface targets such as epidermal growth factor receptors (EGFR). Oligonucleotides produced by chemical synthesis have a promising therapeutic potential and are currently evaluated in clinical trials for the treatment of diseases of eyes, blood, and cancer. (Keefe A. D., Schaub R. G., Aptamers as candidate therapeutics for cardiovascular indications, Curr. Opin. Pharmacol. 2008, Apr., 8(2), pp. 147-52, Epub Jan. 28, 2008; Barbas A. S., Mi J., Clary B. M., White R. R., Aptamer applications for targeted cancer therapy, Future Oncol., 2010, July, 6(7), pp. 1117-26)

Most of chemically synthesized oligonucleotides are subject to nuclease-mediated degradation by serum nucleases, renal filtration, uptake by the liver, spleen, and other tissues. Therefore, the half-life period of oligonucleotides which are not protected by modified nucleotides is not exceeding 2 minutes. Although it is quite a work-consuming process, nucleotides can be specifically modified and protected at the 3' terminus against the action of serum nucleases. (Floege J. et al., Novel approach to specific growth factor inhibition in vivo antagonism of platelet-derived growth factor in glomerulonephritis by aptamers, American Journal of Pathology, 1999, 154, pp. 169-179; Beigelman, L. et al., Synthesis and biological activities of a phosphorodithioate analog of 2',5'-oligoadenylate, Nucleic Acids Res., 1995, 23, pp. 3989-3994) This strategy permits to prolong the serum half-life of these oligonucleotides about 10-fold. To retard renal elimination oligonucleotides are conjugated with polyethylenglycol (PEG) with high molecular weight. In a mouse model non-conjugated oligonucleotides are eliminated from blood with a half-life of 5-10 min., while a 40 kDa PEG conjugates persist in circulation with a half-life of I day. (Burmeister, P. E. et al., Direct in vitro selection of a2'-O-methyl aptamer to VEGF. Chem. Biol., 2005, 12, pp. 25-33)

To date there are several chemically synthesized oligonucleotides that have progressed through clinical evaluation and are currently under review. In December 2004 the first chemically synthesized oligonucleotide Pegaptanib was approved by the US Food and Drug Administration for therapeutic use and is currently marketed by Pfizer and Eyetech as Macugen®. It is an oligonucleotide having a vascular endothelial growth factor (VEGF)-binding sequence of 27-nucleotides. It is administered at 6-week intervals by intravitreal injections for improvement in visual acuity in patients with age-related macular degeneration. (Chakravarthy, U. et al., Year 2 efficacy results of 2 randomized controlled clinical trials of pegaptanib for neovascular age-related macular degeneration, Ophthalmology, 2006, 113, e1-e25).

REG1 is an oligonucleotide having a 34-nucleotide IXa coagulation factor-binding sequence. Currently it is evaluated in phase 2 clinical trials. It shows rapid onset of anticoagulation in viva after intravenous administration, and rapid reversal of anticoagulation effect with return to initial level with antidote RB007. (Chan M. Y. et al., Phase 1b randomized study of antidote-controlled modulation of Factor IXa activity in patients with stable coronary artery disease circulation, 2008, 117, pp. 2865-2874)

ARC1905 is a 39-sequence oligonucleotide, currently evaluated in phase 1 clinical trials. It is used in combination with ranibizumab (which is a VEGF-specific monoclonal antibody fragment) for the treatment of age-related macular degeneration. (Biesecker G., et al., Derivation of RNA aptamer inhibitors of human complement C5, Immunopharmacology, 1999, 42, 1-3, pp. 219-230)

As most of these agents belong to protein inhibitors, their final success depends on their ability to compete with other classes of therapeutic agents, in particular, with monoclonal antibodies which are currently being evaluated along with the most of oligonucleotides in preclinical studies. Moreover, oligonucleotides are characterized by high specificity to target proteins. Each oligonucleotide is capable of inhibiting only one specific protein; this makes them very unreliable agents for the treatment of viral diseases. Viruses are known to develop resistance to specific inhibitors, therefore the perspective of use of such highly specific oligonucleotides for the treatment of viral diseases is doubtful.

Yeast-derived RNA molecules have been long used as therapeutic agents. (Zemskov V. M., Lidak M., Zemskov A. M., Mikstays U. Ya., Small RNA. Preparation, hydrolysis and its application in medicine, Riga, Zanatne, 1985, p. 191) However, in this case a' sodium salt of yeast-derived RNA is used. It is not purified, and is characterized by high molecular weight heterogeneity (as it contains the whole spectrum of nucleotide components from dinucleotides to small transport-RNAs). It also possesses immuno-modulating properties. (Zemskov A. M., Perederiy V. G., Zemskov V. M., Bychkova N. G., Immunocorrective nucleic acid drugs and their clinical application, Kiev, Healthy, 1994, p. 232). Yeast-derived RNA is known to be used for wound healing. (Kulkarni et al., Ribonucleotide preparations and uses thereof—U.S. Pat. No. 5,712,256, Jan. 27, 1988) However, in this case, products of RNA hydrolysis are used (not RNA per se as a certain sequence or secondary configuration). A highly purified yeast-derived RNA with homogeneous molecular weight was suggested for the treatment of inflammation and inflammation-related disorders. (Tkachuk Z., Compound, composition and method for the treatment of inflammatory and inflammatory-related disorders, U.S. Pat. No. 6,737,271, May 18, 2004) Based on this substance, the therapeutic agent Nucleinat was created. It has successfully completed phase 2 of clinical evaluation and has proved to be an effective anti-inflammatory agent for the treatment of acute and chronic pulmonary inflammatory disorders, inflammations of kidneys, and other inflammatory diseases. However, highly purified yeast-derived RNA is devoid of specific antiviral activity. Till now nucleic acids, and, in particular, RNAs have not been used as specific antiviral agents with multiple antiviral action.

The Influenza Viruses.

Influenza virus belongs to the orthomyxoviridae family, and has three serotypes: A, B and C. Serotype A and B viruses belong to the same genus, while serotype C viruses represent a different genus. Each serotype is characterized by its own set of antigenic characteristics which are determined by nucleoproteins (NP) and matrix (M) protein antigens. Type A influenza viruses are widely prevalent in nature and can affect humans as well as some mammals and birds. Type B influenza viruses are isolated only from humans, while type C viruses can be isolated from both humans and pigs. Type A and B viruses are responsible for the yearly flu epidemics. Serotype A consists of subtypes which are characterized by different hemagglutinin (H) and neuraminidase (N) properties. Serotype A viruses and, to a lesser extent, serotype B viruses are characterized by frequent variations of antigenic structure under natural conditions. Antibody response to subtype-specific hemagglutinin is the cornerstone of influenza immunity. Currently there are 15 known subtypes of hemagglutinin (H) and 10 subtypes of neuraminidase (N) of type A influenza viruses circulating in vertebrates. Virological, immunological and seroarcheological studies show that since 1889 epidemics and pandemics have been caused by viruses containing hemagglutinin H1, H2 or H3, and neuraminidase N1 or N2. These viruses have been classified into three subtypes of human A influenza virus designated as A (H1N1), A (H2N2), and A (H3N2). They are responsible for influenza outbreaks with predictable cyclic recurrences of the same virus strains. Viruses replicate in the epithelium of nasopharyngeal and upper respiratory tract mucosa, and produce a potent toxin affecting blood vessels and capillaries.

During epidemics, the virus of influenza attacks a great number of people, influencing negatively the economies of countries. Therefore, search for and the use of chemotherapeutic drugs capable of blocking the virus reproduction becomes very important. Until recently, effective chemoprophylaxis of influenza, as well as other virus diseases was very complicated. The first mentioning on antiviral action of 1-amino-adamantane was done in 1963 by Jackson and co-authors. (Jackson G. G., Muldon R. L., Akers L. W., Serological evidence for prevention of influenza infection in volunteers by anti-influenzal drug amantadine hydrochloride, in Antimicrobial agents and chemotherapy, S. I., Acad. Press, New York, 1964, pp. 703-707). In 1964 Device and co-authors published the results of experiments (Davies W. L., Grunert R. R., De Somer P. et al., Antiviral activity of 1-adamantanamine (amantadine), Science, 1964, 144, pp. 862-863) Remantadine became the first drug, which was widely used for the prevention and treatment of influenza.

In 1970, the crystal structure of viral neuraminidase of flu A and B types was discovered and it was proved that inhibiting the neuraminidase component of influenza virus delays the reproduction of virus. (Miller W. E., Mechanisms of action and pharmacology chemical agents, in Antiviral agents and viral diseases of man, Ed. by G. J. Gallasso et al., Raven Press, New York, 1979, pp. 77-149; Hay den F. G., Osterhaus A. D., Treanor J. J. et al., Efficacy and safety of the neuraminidase inhibitor zanamivir in the treatment of influenza virus infections, in GG 167 Influenza Study Group, N. Engl. J. Med., 1997, 337, 13, pp. 874-880) This allowed creating drugs that block the activity of neuraminidase of A and B virus types—oseltamivir and zanamivir. These drugs protect from infecting the epithelial cells of respiratory tract and prevent spreading of the virus in body. Oseltamivir and zanamivir showed high preventive and treatment effectiveness with a decreased period of treatment by 2-3 days on average and an easier course of disease. [Monto A. S., Fleming D. M., Henry D. et al., Efficacy and safety of the neuraminidase inhibitor zanamivir in the treatment of influenza A and B virus infections, J. Infect. Diseases, 1999, 180, 2, pp. 254-261; Iozzo M., Efficacy and tolerability of the neuraminidase inhibitor Zanamivir, J. Acad. Phys. Assistants, 2001, 2, 2, pp. 186-188; Hoyden F. G., Treanor J. J., Fritz R. S. et al., Use of oral neuraminidase inhibitor Osettamivir in experimental human influenza, J. Amer. Med. Assoc., 1999, 282, 13, pp. 48-50)

The epidemics of influenza and acute respiratory virus infections are accompanied by high death rate and serious complications in the vulnerable population groups. The risk group includes people with chronic conditions, especially cardio-vascular diseases. (Davis M. M., Taubert K., Benin A. L. et al., Influenza vaccination as secondary prevention for cardiovascular disease: a science advisory from the American Heart Association, Amer. College of Cardiology, Circulation, 2006, 114, pp. 1549-1553)

There is convincing evidence that acute respiratory virus infections and influenza cause heart attacks and it was proved that drugs against viral infections are an effective method for decreasing the risk of heart attacks in people with cardiovascular diseases. (Warren-Gash C, Smeeth L., Hayviard A. C., Influenza as a trigger for acute myocardial infarction or death from cardiovascular disease: a systematic review, Lancet Infect. Dis., 2009, 9, pp. 601-610)

Epidemics of influenza and ARVD are accompanied by heavy mortality and dangerous complications among vulnerable set of men. To the population at risk belong people with chronic pathologies, especially with such as cardiovascular diseases. (Davis M. M., Taubert K., Benin A. L. et al., Influenza vaccination as secondary prevention for cardiovascular disease: a science advisory from the American Heart Association, American College of Cardiology, Circulation, 2006, 114, pp. 1549-1553) Yet, the connection between contagion with ARVD and influenza and the acute myocardial infarction remained unclear for long. Different works reported the seasonality of cardiovascular mortality models, what reminded models of ARVD and influenza circulation. (Ailing D. W., Blackwelder W. C., Stuart-Harris C. H., A study of excess mortality during influenza epidemics in the United States, 1968-1976, Am. Epidemiol., 1981, 113, pp. 30-33; Collins S. D., Excess mortality from causes other than influenza and pneumonia during influenza epidemics, Public Health Rep., 1932, 47, pp. 2159-2179; Eickhoff T., Sherman I, Serfling R., Observations on excess mortality associated with epidemic influenza, JAMA, 1961, 176, pp. 776-782; Housworth J., Langmuir A. D., Excess mortality from epidemic influenza, 1957-1966, Am. J. Epidemiol., 1974, 100, pp. 40-48)

Clinical scores in patients with influenza pointed to the definitive systemic impacts, such as high temperature, muscle pain and fatigue, and also indicated frequent myocardial ischemia episodes. (Greaves K., Oxford J. S., Price C. P., Clarke G. H., Crake T., The prevalence of myocarditis and skeletal muscle injury during acute viral infection in adults: measurement of cardiac troponins I and T in 152 patients with acute influenza infection, Arch. Intern. Med. 2003, 163, pp. 165-168; Ison M. G., Campbell V., Rembold C., Dent J., Hayden F. G., Cardiac findings during uncomplicated acute influenza in ambulatory adults, Clin. Infect. Dis., 2005, 40, pp. 415-422; Paul B. K., Clinical observations of influenza, with special reference to its effects and cardiac functional efficiency, Indian Med. J., 1963, 57, pp. 251-283; Verel D., Warrack A. J., Potter C. W., Ward C., Rickards D. F., Observations on the A2 England influenza epidemic: a clinico-pathological study, Am. Heart J., 1976, 92, pp. 290-96) These results led to the inference that influenza can play a role of an acute inflammatory stimulus, which triggers cardiovascular incrusions. In order to prognose risk of vascular diseases in humans markers of systemic inflammation and inflammatory cells activation came to be used as an important component of It is known that influenza virus greatly affects inflammatory, coagulation and metabolic pathways (Madjid M., Aboshady I., Awan I., Iitovsky S., Casscells S. W., Influenza and cardiovascular disease: is there a causal relationship, Tex. Heart Inst. J., 2004, 31, pp. 4-13), which can lead to atheromatous plaque destabilization and thereby to the partial occlusion or the complete obturation of the coronary vessel, which is the main cause of the acute infarction. (White H. D., Chew D. P., Acute myocardial infarction, Lancet, 2008, 372, pp. 570-584) Moreover, influenza can act as an acute inflammatory and pro-coagulator stimulus of the rapid changes in the endothelium. (Housworth J., Langmuir A. D., Excess mortality from epidemic influenza, 1957-1966, Am. J. Epidemiol. 1974, 100, pp. 40-48; Madjid M., Awan I., Ali M, Frazier L., Casscells S. W., Influenza and atherosclerosis: vaccination for cardiovascular disease prevention, Expert Opin. Bid. Ther., 2005, 5, pp. 91-96) Well known are heart complications as a result of influenza infection, such as myocarditis, pericarditis, yet the influenza role under the character of the trigger mechanism of acute myocardial infarction is not clearly proved. At the same time in the task-specific literature emerged many facts of that the influenza (including influenza as a disease and a acute respiratory infection) can precipitate acute myocardial infarction or even vascular death. Numerous investigation, conducted at different conditions, using different methods indicate that there is a tight connection between influenza and acute myocardial infarction. At the same time there are not many clinical studies, which would investigate the possibility of risk reduction of cardiovascular complications by using antiviral and cardioprotective medications in patients with influenza and ARVD. Only in two small randomized investigations was estimated a positive impact of anti-influenza vaccination on the prevention of heart seizures in patients with cardiovascular diseases and it was shown that vaccination against influenza results in considerable protection against vascular death. Obtained summarized valuation of the model of randomized consequences intends whilst insignificant, still protective effect of vaccination. Authors consider that in cases, where it was shown, anti-influenza vaccination should be encouraged, especially in people with cardiovascular diseases, which are often of prejudged oppositional code of vaccination. (Warren-Gash C, Smeeth L, Hayviard A C. Influenza as a trigger for acute myocardial infarction or death from cardiovascular disease: a systematic review, Lancet Infect. Dis., 2009, 9, pp. 601-610)

Thus, there is a luculent proof of the fact that influenza can provoke development of acute myocardial infarction, increase vascular death, but the usage of anti-Viral medications can be an effective way to reduce the rick of heart seizures in patients with cardiovascular diseases.

The Hepatitis Viruses

According to World Health Organization (WHO), hepatitis is defined as inflammation of the liver caused by infectious or toxic agents. In most cases it is caused by one of the five viral agents: hepatitis A virus (HAV), hepatitis B virus (HBV), hepatitis C virus (HCV), the HBV-associated delta agent or hepatitis D virus (HDV), and hepatitis E virus (HEV).

Hepatitis A is an acute infectious disease predominantly affecting the gastrointestinal tract, particularly the liver. Hepatitis A is caused by hepatitis A virus which is spread through contaminated food or water. Persons with acute hepatitis A are the source of infection. The disease is dangerous as it leads to liver cell death and liver function impairment.

Hepatitis B is caused by hepatitis B virus (HBV) which affects the liver by causing its inflammation. About 600,000 people worldwide die each year of hepatitis B-related complications. HBV is transmitted from infected persons through blood or other body fluids like semen, vaginal secretions, and saliva. The modes of transmission of hepatitis B virus are the same as those of human immunodeficiency virus (HIV), but compared with the latter the HBV infectivity is 50-100-fold higher. Unlike HIV, HBV can resist in the environment beyond human organism for at least 7 days.

Hepatitis D. Hepatitis D is caused by hepatitis D virus (or delta virus) and is characterized by acute onset with massive liver cell damage. Delta virus is unable to replicate on its own, it requires the presence of HBV for its replication and expression. Hepatitis D follows a similar mode of transmission as hepatitis B and hepatitis C. Its incubation period is 3 to 7 weeks. Clinical manifestations of hepatitis D are similar to those of hepatitis B. Vaccination against hepatitis B also prevents hepatitis D.

Hepatitis E. Hepatitis E is similar to hepatitis A in its symptoms. The modes of transmission of hepatitis E are also similar to those of hepatitis A. Hepatitis E is spread through contaminated water or food, and can also be transmitted through blood. It occurs primarily in Central Asia and in African countries.

Other agents, such as hepatitis F virus and hepatitis G virus have been recently identified, but as yet have not been studied extensively.

Hepatitis C is a viral infection with parenteral mode of transmission occurring most frequently in the form of post-transfusion hepatitis. HCV was discovered in 1989 in patients with hepatitis whose blood contained a viral RNA similar in organization to that of flaviviruses. Hepatitis C is caused by an RNA-containing virus of the family Flaviviridae. Its virion is estimated to be 30 to 60 nm in diameter. To date up to 11 distinct genotypes of HCV have been identified: 1a, 1b, 1c 2a, 2b, 2c 3a, 3b 4a, 4b, 4c, 4d, 4e 5a 6a 7a, 7b 8a, 8b 9a 10a 11a. HCV consists of structural (capsid and envelope) and non-structural viral proteins, and tends to circulate in blood in low titer. It is associated with low density lipoproteins and anti-bodies to HCV proteins. The sources of infection are patients with manifest and latent forms of hepatitis C. The virus is transmitted by parenteral route through blood and blood products. The current standard of treatment of hepatitis C, approved in a number of countries, is a combination antiviral therapy with alpha interferon and ribavirin. It is indicated in HCV-RNA-positive patients with persistently elevated serum ALT levels and marked histological liver damage. The duration of therapy may range from 12 to 72 weeks, depending on HCV genotype and on the response to treatment determined by the individual patient characteristics and host's genome. The current criteria of effectiveness of hepatitis C therapy include a sustained biochemical remission (persistent normalization of alanine aminotransferase levels after antiviral therapy), and absence of viremia (i.e., clearance of HCV RNA at 6 months after the end of therapy).

Hepatitis C Virus is a global health problem. Its agent is an RNA-containing virus, which is transmitted orally and causes an acute or permanent hepatitis, which can lead to cirrhosis or liver cancer in 60-80% cases. In accordance with the information of WHO, about 1% of world population are infected with Hepatitis C Virus (HCV). The source of infection is a human; in 100% of cases, the virus can be found in the blood of an infected patient. Hepatitis C Virus is called <<the silent killer>>. In 70% of cases the illness is taking a latent form. Regardless of the severance, in 50-80% cases Hepatitis C Virus transforms into a permanent illness with the consequential development of cirrhosis, carcinoma, damages neural cells, causes severe consequences.

The virus is categorized under the type Hepatitis C-like viruses of the Flaviviridae family (Alter Y. J., To or not to C: these are questions, Blood, 1995, 85, pp. 1681-1695; National Institutes of Health Consensus Development Conference Panel Statement: Management of Hepatitis C, Hepatology, 1997, 26, pp. 2-10), contains a positive polarity RNA (Lindsay K. L., Therapy of hepatitis C overview, Hepatology, 1997, 26, pp. 715-775), which has a high degree of heterogeneity. (Yohko K. S., Hiroshi Y., In vitro systems for the detection of hepatitis C virus infection, Viral Hepatitis Rev., 1995, 1, pp. 59-65; National Institutes of Health Consensus Development Conference Panel Statement: Management of Hepatitis C, Hepatology, 1997, 26, pp. 2-10) α-Interferon remedies (IFN)—reaferon, roefron A, intron A, and others—remain to be the basis for the treatment of HCV-infection (EASL International Consensus Conference on Hepatitis C. Consensus Statement. Paris, J. Hepatol., 1999, 30, pp. 976-995), however, the reliable anti-virus effect (absence of HCV RNA in the blood serum 6 month after the treatment) can be observed only in 8-12% of patients treated with a-Interferon. (Lindsay K. L., Therapy of hepatitis C^overview, Hepatology, 1997, 26, pp. 715-775) Therefore, the search for alternative ways of therapy of the HCV infection remains important nowadays.

IFN inductors, which represent a diverse group high- and low-molecular natural and synthetic compounds, which are related by their ability to cause IFN production, is a perspective group for the treatment of virus infections, including HCV. IFN inductors have typical, for IFN, antivirus, antiproliferative, and immune-modulating activities (Ershov F. Y., Anti-virus Pharmaceuticals, Moscow, 1998, p. 240)

The vaccine against HCV has not been developed yet, and there are no effective drugs capable of inhibiting the virus replication in body. The difficulties with finding preventive and treatment medications against HCV are related to the unsuccessful attempts to obtain an experimental model of the virus required for screening tests for identification of the drugs, which can effectively treat HCV.

Herpes viruses

Herpesvirus (Latin Herpesviridae) is a large family of DNA-containing viruses that cause various diseases not only in humans and other mammals, but birds, reptiles, amphibians, fish. Herpes viruses infected the majority of the population of our planet. (Baltimore D. The strategy of RNA viruses, Harvey Lect., 1974, 70 Series, pp. 57-74)

Herpetic infection is a classic example of a latent infective process. Above 70% of patients suffered recurrences of infection after the first contact with herpes simplex virus (HSV) regardless of high antiherpetic antibody levels. Herpetic infections represent a group of anthropozoonotic infectious diseases caused by human herpes viruses (HHV) with varying types of clinical course, comprising unapparent, subclinical and manifest clinical forms. (Liesegang T., Herpes simplex, Cornea, 1999, Vol. 18, No. 6., p. 739)

Herpes (Greek origin meaning "creeping") is one of the most prevalent and poorly controlled human infections. In a host with the normal immune system herpetic viruses may circulate asymptomatically, while in immunocompromised individuals they may cause severe potentially lethal. In humans 8 types of herpes viruses have been identified: these are represented by DNA-containing viruses with similar morphology which are indistinguishable on electron microscopy. (Herpesviruses, in: Baron's Medical Microbiology, Baron S et al., Eds., 4th.; U. of Texas Medical Branch, 1996; Medical Microbiology, 5th Ed., Elsevier Mosby, 2005) Entering a human organism, a herpes simplex virus (HSV) infects its host forever causing occasionally recurrences of varying. HSV in its latent state is localized in paravertebral sensor ganglia in the form of L-PREP-particles.

The most common human herpes virus (HHV) is the type 1 herpes simplex virus, or HSV-1, causing orofacial herpes. Similar morphological, antigenic, chemical, and physical properties are shared by type 2 human herpes virus (HSV-2 or HHV-2) causing genital herpes. Genital herpes (GH) is a particular herpetic infection, representing one of the most prevalent sexually transmitted disease. Its prominent feature is that the causative agent will remain with the carrier for the rest of his/her life (latency). This is the reason for the high incidence and frequent recurrences of the disease.

The onset of GH is often associated with HSV-2. This is supported by the high incidence of antibodies (Ab) to this virus serotype found in epidemiological. Previously it has been considered that HSV-1 is more frequently identified in skin infections involving face, trunk and upper limbs. Now it is well established that GH may be caused by HSV-1. HSV-1-caused GH is characterized by low recurrence rates, the recurrences are more frequently observed in patients with high titers of anti-HSV-2 antibodies. This virus plays a role in pathogenesis cervical cancer as demonstrated by means of hybridization of HSV DNA with the DNA of tissues obtained during surgeries for cervical cancer and cervical canal malignancies.

Type 3 human herpes virus (HHV-3) causes two different clinical entities—varicella zoster and herpes zoster. Type 4 human herpes virus (HHV-4), or Epstein-Barr virus, is a causative agent of infectious mononucleosis, Burkitt's lymphoma, nasopharyngeal carcinoma, hairy tongue leukoplakia. Type 5 human herpes virus (HHV-5) causes cytomegalovirus infection, and finally, type 6 human herpes virus (HHV-6), according to recent studies, is associated with exanthema subitum in infants and chronic fatigue syndrome in adults. Current literature reports indicate that HHV-6 may play a role in development of lymphogranulomatosis, malignant. B-cell lymphoma, sarcoidosis, Sjogren's syndrome, Crohn's disease, autoimmune thyroiditis, non-Epstein-Barr virus infectious mononucleosis. It may cause acute hepatitis in children and adults, including fulminating hepatitis with lethal outcome. In 1990 HHV-7 and HHV-8 were discovered, their role is yet to be established. HHV-7 is associated with lymphoproliferative disorders and chronic fatigue syndrome, while HHV-8 is associated with Kaposi sarcoma.

Treatment of herpetic infection is still challenging. A long-lasting chronic process leads to negative regulation of the immune system. Secondary immunodeficiency, suppression of cell-immunity and decrease of non-specific resistance are observed, manifesting as decreased ability of white blood cells to synthesize $\alpha$- and $\gamma$-interferons (IFN), hypoimmunoglobulinemia, sensitization to viral antigens. (Herpesviruses, in Baron's Medical Microbiology, Baron S et al., Eds.; 4th U. of Texas Medical Branch, 1996; Medical Microbiology, 5th Ed., Elsevier Mosby, 2005)

Currently antiherpetic drugs constitute around 80% of the available antiviral agents re-emphasizing the importance of the problem. Most of them are represented by anomalous nucleosides. The mechanism of their action combines the inhibition of enzymes involved in viral replication (thymidine kinase, DNA-polymerase) with the induction of IFN synthesis. Hence is the question: why despite a significant number and variety of antiviral agents, herpetic infections are still poorly controlled? Recent reports indicate that resistance of HSV to antiherpetic anomalous nucleosides is increasing over the past years.

However the most efficient way is the development of antiviral agents capable of affecting the early stages of viral replication, namely adsorption and merging with cells. Novel antiviral agents are being modeled as ligand imitators or receptor imitators capable of competitive substitution of the natural components while interacting with the host cell. The aim of the present study was to assess the efficacy of antiviral action of RNA preparations possessing the above-mentioned properties.

Human Immunodeficiency Virus

The first case of acquired immunodeficiency syndrome (AIDS) was reported in the USA in 1983. The patient died 2 months later. Currently around 14,000 of new infections occur daily. The causative agent is a virus with a helical structure within a triangular core. It is known as human immunodeficiency virus (HIV) and has three types: HIV-1 and HIV-2 which are highly prevalent in Western Europe, and HIV-3 which is prevalent mostly among Africans and Americans. The virus infects T-lymphocytes which serve for its replication, and macrophages which spread the virus through the organism. AIDS per se is not a fatal disease, but HIV down regulates the immune system of the human organism so that even a common cold may lead to death. HIV destroys T-lymphocytes and the human organism loses its defense mechanisms resulting in increased vulnerability to ordinary infections. The risk of fatal infections, nervous system involvement, and cancer increase dramatically. The source of infection is an HIV carrier. Transmission is possible during sexual intercourse with an HIV-infected person or by blood to blood contact. If an infected mother gives birth to a child, the child is not necessarily a virus carrier. Antiretroviral therapy permits to decrease the risk of mother-to-child transmission to as low as 6 percent. (Sepkowitz K. A., AIDS—the first 20 years, N. Engl. J. Med., 2001, 344, 23, pp. 1764-72; Divisions of HIV/AIDS Prevention HIV and Its Transmission. Centers for Disease Control &Prevention, 2003) The first antiretroviral drug known as azidothymidine was first synthesized in 1964, and in 1987 it was approved for the treatment of HIV-infection and has been widely used as an antiretroviral agent since then. (Balzarini J., Naesens L., Aquaro S., Knispel T., Pemo C.-F., De Clercq E., Meier C., Intracellular metabolism of cyclosaligenyl 3'-azido-2'-3'-dideoxythymidine monophosphate, a prodrug of 3'-azido-2'-3'-dideoxythymidine (Zidovudine), Molecular Pharmacology, 1999, 56, pp. 1354-1361) In the mid-90s, the first protease inhibitors became available, including saquinavir, ritonavir, and indinavir. Their use permitted to decrease mortality from 38 to 22 percent. (Cameron D. W., Heath-Chiozzi M., Danner S., Cohen C, Kravcik S., Maurath C., Sun E., Henry D., Rode R., Potthoff A., Leonard J., Randomised placebo-controlled trial of ritonavir in advanced HIV-1 disease, The Advanced HIV Disease Ritonavir Study Group, Lancet, 1998, 351, 9102, pp. 543-549) In 1996 the first non-nucleoside reverse transcriptase inhibitor nevirapine and another protease inhibitor nelfinavir were introduced. In Europe, the use of new drugs permitted to decrease the AIDS-related morbidity from 30.7 to 2.5 percent. (Harrington M., Carpenter C. C., Hit HIV-1 hard, but only when necessary, Lancet, 2000, 355, 9221, pp. 2147-52)

However, despite a high number of quiet expensive anti-retroviral agents, there is a growing problem of HIV multi-drug resistance. This re-emphasizes the importance of search for new agents targeting at multiple HIV proteins. Of particular importance is the need of new antiviral drugs capable of inhibiting replication of not only HIV, but also of other viruses, e.g., hepatitis viruses which frequently represent a concomitant infection in HIV-positive patients.

Enteroviruses belong to the Picornaviridae family. They encompass 67 serotypes which are pathogenic for humans: 3 serotypes of poliovirus, 23 serotypes of coxsackievinis A, 6 serotypes of coxsackievirus B, and others. Enteroviruses are so named because of their ability to multiply in the gastrointestinal tract. Despite their name, these viruses rarely cause prominent enteritis. Human enteroviruses contain a single-stranded RNA encoding a polyprotein that is cleaved into 11 different proteins. The enteroviral RNA genome is surrounded by an icosahedral capsid comprising four viral proteins (VP1-VP4). VP1 is the predominant target neutralizing antibodies. Enteroviruses have an ubiquitary distribution. Coxsackieviruses are responsible for a broad spectrum of diseases in humans, most commonly, aseptic meningitis and myalgia. These viruses are spread by the fecal-oral route as well as the other enteroviruses. Coxsackieviruses are divided into group A and group B. Group A includes about 24 serotypes causing herpangina, aseptic meningitis, pericarditis, nonspecific febrile illness, and others. Group B is responsible for Bornholm disease (pleurodynia, myalgia). Diseases associated with group A and group B coxsackieviruses have distinct clinical features.

Coxsackievirus B4 affects both central and peripheral nervous system, causing headache (particularly, occipital headache) and chest pain.

The need for new antiviral agents.

Currently, there is a need of development of novel antiviral agents with multiple action against various viral diseases. These agents should interfere with the mechanisms responsible for viral penetration into the host cell and viral release.

The recognition of the possibility of an antibiotic drug, capable of inhibiting many representatives of the virus family was based on the discoveries by Charles Janeway and his followers. (Janeway Jr., C. A., Approaching the asymptote? Evolution and revolution in immunology, Cold Spring Harbor Symposia on Quantitative Biology, 1989, 54, 1, pp. 1-13) First, it was shown that all live organisms possess an innat immunity. This innat immunity exists on the genetic level and provides for the ability of organism to fight alien microorganisms, transplants, toxins, tumor cells, and cells infected with viruses. The system of innat immunity is activated at first emergence of a pathogen and reacts at certain classes of antigens specific for pathogen organisms. Second, the cells of innat immunity possess the receptors called Toll-like receptor, TLR, which recognize these classes of antigens and activate the innat immunity. Third, the TLR is specific to certain class of infections, i.e., is capable to recognize specific type of alien structures, for example, virus infection RNA, rather than general. People have more than ten TLRs, each specializing in certain class of pathogens. One recognizes RNA of virus infections, another—polysaccharides of bacteria, another— proteins of single-cell parasites, etc. The Receptors are located on different types of cells, including the cells of skin and epithelium.

In case of recognition of virus factor, the infected cell with the help of TLR can switch off the synthesis of virus protein, to initiate the programmed death of infected cell (apoptosis). Immune cells which identified the virus can spread signals for the expression of cytokines, factors causing inflammations, and also can emit antivirus factors such as interferon.

SUMMARY OF THE INVENTION

Until now, the action of most antiviral drugs was focused on one specific infectious agent, but viruses used to quickly develop drug resistance. In one aspect, the present invention proposes an RNA-based agent and a method of treatment providing multiple antiviral actions at different stages of viral development. A long-lasting and sustained antiviral action of the RNA-based agent makes impossible rapid development of viral resistance to this kind of agents. As a number of viral diseases are associated with the action of multiple viruses, necessitating the use of multiple antiviral agents, the present invention provides an agent that is active against multiple viruses. For example, acute upper respiratory tract infection is frequently associated with a complex action of influenza and parainfluenza viruses. A similar situation is found in AIDS when HIV is frequently associated with hepatitis viruses. The use of the agent permits to act against several of these viruses.

As previously suggested, RNA-based therapeutic agents have been produced by chemical synthesis, but they are quite expensive from the standpoint of technology and not applicable for the treatment of mass viral diseases. In another aspect, the present invention provides an agent synthesized from a yeast-derived ribonucleic acid which is a cheap natural substance. It may be widely used in the form of capsules, tablets, and other available dosage forms.

Viral infections such as AIDS, hepatitis C, and others require a complex management in combination with antibiotics and other antiviral agents frequently associated with toxicity and neuro-psychiatric side effects. In another aspect, the present invention proposes a non-toxic agent with no side effects due to its long-term use in complex therapy.

In another aspect of the present invention, it was recognized that RNA compounds, which are similar to virus RNA by conformation, are able to activate innate immune system and act as antibiotics with regard to various viruses, which cause severe illnesses in humans, such as pandemic flu, Hepatitis C, genital Herpes, and AIDS. Highly-purified yeast RNA, which underwent temperature treatment, has correspondingly improved properties.

As reported below, a complex study of agents containing a yeast-derived ribonucleic acid (RNA) in different in vitro and in vivo models was performed. The tested models corresponded to specific types of virus-induced process. The action of RNA-containing agents was compared to the action of drugs which are currently approved for antiviral therapy.

1. In Vitro and In Vivo Influenza Viruses Models

The anti-influenza activity in vitro was demonstrated on re-inoculated MDCK cell line (canine renal cells) with a confluent layer according to existing guidelines. (Preclinical drug research: guidelines, Kyiv, 2001, pp. 371-396) Anti-influenza activity in vivo was studied on a model of influenza pneumonia in mice with the use of prophylactic and therapeutic regimen of administratiOn.

Thus, it has been demonstrated that an RNA-based drug is an anti-influenzal medicine.

In an particular embodiment, a maximum tolerated concentration is 5,000 mkg/ml, and a minimum active concentration is 31 mkg/ml; the chemotherapeutic index constitutes 161.

An effective dose of a combination RNA extract—sugar, with the sugar being, for example, mannitol (RNA-M) calculated in vitro is advantageously 1.25-10 mg/ml for preventive purposes and 0.6-10 mg/ml for therapy. A high anti-influenzal activity of the drug has been demonstrated in prevention treatment in mice for intra-abdominal and intra-venous introduction in dosages between 15 and 150 mg/kg. In case of intranasal introduction, an effective dose is, for example, at least ten times higher. In has been determined that anti-influenzal action RNA-M lies in inhibition of neuraminidase and hemagglutinin during the interaction with the influenza virion. Also a combination RNA extract—sugar is a prolonged inductor of alpha-interferon in in vivo tests. The dose of administration is calculated on the amount of RNA in the compound.

Thus, the in vitro and in vivo models used for evaluation of anti-influenza agents have demonstrated that a yeast-derived RNA-containing agent is characterized by a potent antiviral activity. With regard to its anti-neuraminidase and anti-hemagglutinin activity, this agent may be considered as possessing a specific anti-influenza activity.

2. In Vitro and In Vivo Hepatitis Viruses Models

In another aspect of the present invention, anti-HCV activity of yeast RNA-derived drugs was demonstrated on an experimental model of MT-4 suspension cell culture infected with hepatitis C virus (HCV), and also on a new model of producing cell culture transfixed with HCV cDNA (MT-4—HCV cDNA model), and on a surrogate test-model of HCV and bovine viral diarrhea virus (BVDV).

It has now been discovered that an RNA-based drug is highly effective against HCV, in particular human HCV.

The results of studies on the effectiveness of a preparation containing essentially a purified RNA extract, for example, from yeast, combined with a sugar, for example, mannitol, on the culture model MT-4 infected with cultured human HCV showed that, in an advantageous embodiment of the RNA-based drug, its maximum tolerance concentration equals 50 mg/ml, the minimum active concentration is 0.25 mg/ml, and the chemotherapeutic index is 200.

The results of studies on antivirus activity of a preparation containing essentially a purified RNA extract, for example, from yeast, combined with a sugar, for example, mannitol, on the model MDVK-BVDV show that in the concentration of at least about 1 mg/ml, the drug inhibits virus reproduction by 2.0 lg ID50, while in the concentration of at least about 0.5 mg/ml—correspondently by 3.0 lg ID50.

In summary, RNA-M preparation can be classified as a highly effective antivirus drug capable of inhibiting the reproduction of human HCV.

The experimental results also demonstrated a purified RNA extract, for example, from yeast, combined with a sugar, for example, mannitol, has a beneficial use in therapy of HCV. Namely, high efficiency was confirmed for treatment of patients with hepatitis C. The improvement of feel of patients, stabilizing of biochemical indexes, decline of amount of copies of virus, is marked in the serum of blood. The composition was tolerated well, side effects were not registered.

3. In Vivo Herpes Viruses Models

The in vivo study of prophylactic and therapeutic action of RNA-M was performed on a rabbit kidney cell line (RK13). The in vivo study of RNA-M antiherpetic action was studied in a model of murine herpetic meningoencephalitis caused by herpes simplex virus (HSV-1), as well as in a model of genital herpetic infection in guinea pigs infected by HSV-2. Cytological analysis was performed in HSV-sensitive cells of rat gasserian ganglion neurinoma.

It has now been discovered that a RNA-based drug has a potent antiherpetic action.

In particular, a preparation containing essentially a purified RNA extract, for example, from yeast, combined with a sugar, for example, mannitol, proved to be an active antiherpetic agent. In vitro, in an advantageous embodiment, its virus-inhibiting activity lies within the range of 60 to 1,000 mcg/ml, its minimal active concentration (MAC) is 60 mcg/ml, maximum tolerance concentration (MTC) is 5,000 mcg/ml, and its chemotherapeutic index is 83.3.

The in vitro effectiveness of a preparation containing essentially a purified RNA extract, for example, from yeast, combined with a sugar, for example, mannitol, in prophylactic and therapeutic regimens of administration is within a broad range of concentrations from 0.6 to 10 mg/ml. Such preparation in prophylactic dose of 0.1 mg/ml and in therapeutic dose of 1 mg/ml did not adversely affect the mitotic index nor the count of pathological mitoses.

In particular, in a model of herpetic meningoencephalitis the therapeutic regimen of intraperitoneal administration of 0.5 mg/kg of a combination RNA-mannitol (RNA-M) resulted in the effectiveness index of 41.2. In a particularly effective embodiment, RNA-M was used topically in a model of genital herpes. In prophylactic regimen of administration of 0.1 mg/ml of RNA-M and in therapeutic regimen of administration of 1.0 mg/ml of RNA-M, the therapeutic activity index (TAT) constituted 100% and 73.2%, respectively. In animal studies RNA-M appeared to be surprisingly superior to Virolex® used as the referent agent.

The in vitro and in vivo models which are used for selection of antiherpetic agents permitted to conclude that a combination of a purified RNA extract, for example, from yeast, combined with a sugar, for example, mannitol, possesses a potent antiherpetic action.

In particular, effectiveness in the treatment of Herpes virus disease, especially genitals herpes treatment, was demonstrated.

4. In Vivo AIDS Viruses Models

In an aspect of the present invention, it is demonstrated that a purified RNA extract, for example, from yeast, combined with a sugar, for example, mannitol, is effective in inhibiting HIV reproduction.

In particular, administration to HIV-infected persons resulted in the decline of level of the viral loading of HIV and increase amount of $CD4^+$ T-lymphocytes.

5. In Vivo Enteroviruses Models

In an aspect of the present invention, it is demonstrated that a purified RNA extract, for example, from yeast, combined with a sugar such as mannitol, is as an active antiviral agent, with high anti-enteroviral activity.

6. Composition and Administration

Generally, administration may be at least about 0.1 mg/kg/day for prevention, and at least about 10 mg/kg/day for treatment, of the purified RNA compound after the temperature processing with sugar, along with at least one of pharmaceutically acceptable vehicles, carriers, fillers, and diluents, for example. Further, the dose of administration is calculated on the amount of RNA in the compound.

For influenza prevention, intra-abdominal or intravenous administration is preferably from about 1.5 to about 10 mg/kg/day, and intranasal administration is preferably at least about 2.5 mg/kg/day, more preferably at least about 25 mg/kg/day.

For influenza treatment, intra-abdominal or intravenous administration is preferably from about 1.5 to about 25 mg/kg/day, and intranasal administration is preferably from about 2.5 to about 25 mg/kg/day, more preferably at least about 50 mg/kg/day.

An effective dose to decrease hemagglutination is preferably at least about 1 mg/ml, more preferably at least about 10 mg/ml.

AN effective dose to inhibit HCV reproduction in tissue culture is preferably at least about 0.25, more preferably at least about 0.5 mg/ml.

An effective dose for prophylactic and therapeutic regimens of antiherpetic agent is within a broad range of concentrations from 0.6 to 10 mg/ml.

An effective dose in prophylactic and therapeutic regimens of administration is within a broad range of concentrations from about 0.1 to about 10 mg/ml of the combination of purified RNA extract, for example, from yeast, with a sugar, for example, mannitol, in particular prophylactic doses as low as from about 0.1 to about 1.0 mg/ml, and therapeutic doses as low as from about 1.0 mg/ml to about 10 mg/ml. Prophylactic dose of 0.1 mg/ml and therapeutic dose of 1 mg/ml did not adversely affect the mitotic index nor the count of pathological mitoses.

For example, an effective treatment dose of the drug is 5-10 mg of RNA per 1 kg per day. The duration of antivirus treatment is advantageously from 7 days for ARVI to at least about 3-5 months for herpes viruses and up to 1.5 years or more for hepatitis C virus. An exemplary product ready for oral administration is in the form of an orally ingestible tablet or capsule containing 250 mg of yeast RNA and 100 mg mannitol.

BRIEF DESCRIPTION OF THE FIGURES

FIGS. 1-10 are graphs measuring the dynamics of the mean values of subjective complaints and objective symptoms of disease, respectively (1) high body temperature, (2) headache, (3) catarrhal signs, (4) general weakness, (5) joint pain, (6) mialgia, (7) pruritus and burn in the nasal ducts, (8) fatiguability, (9) fever, and (10) sore throat.

FIGS. 11-14 are comparative diagrams showing response between a test and a control groups in patients subgroups, infected with different viruses, respectively (11) influenza virus (12) influenza virus B, (13) parainfluenza virus, and (14) adenovirus, according to the primary variables (i) time of temperature normalization, (ii) time of headache relief, and (iii) time of the general weakness relief.

FIG. 15 shows the results of electrophoresis for small RNA in 15% PAAG, containing DS-Na and 7M urea, drugs: E. Coli TRNA (stripe-1, sector-a), 25-member oligonucleotide (stripe-1, sector-b), highly purified yeast RNA (stripe-2), sodium salt of yeast RNA (stripe-3).

DETAILED DESCRIPTION OF PARTICULAR EMBODIMENTS

Example 1

Example of Method for Obtaining Antiviral RNA

Example 1.1. Extraction, Purification and Analysis of RNA

In one aspect, the RNA-based drug contains a purified RNA extract, for example, a yeast RNA. Two types of yeast, *Saccharomyces cerevisiae* and *Candida utilis*, can be advantageously used for the extraction and purification of yeast RNA. In this respect, industrial yeast RNA compounds extracted from these two types of yeasts can be used, as shown herein, but the RNA extract can be obtained from other sources, provided it meets the requirements for antiviral effectiveness as described herein.

Respective criteria on molecular mass and purity of the RNA extract are preferred: with regard to the molecular mass, it is preferred that the RNA consists mainly of fragments having 25±10 nucleotides, which corresponds to a range of from about 4200 to about 9800 for molecular mass. Particular embodiments will consist mainly of fragments having 25±5 nucleotides, or, for example, of fragments having 25±2 nucleotides, advantageously, of fragments having 25 nucleotides. For example, the RNA extract contains substantially at least 75% by weight of oligonucleotides having a molecular mass of from about 4200 to about 9800, more preferably substantially at least 90% by weight of fragments having from 20 to 25 nucleotides, of the total yeast RNA extract. Preferably, the proportion with respect to any of the above nucleotide number ranges or the molecular mass range, or both, is at least 75% by weight, more preferably at least 90%, furthermore preferably at least 95%, even more preferably substantially 100%, for example, at least 99%. Advantageously, one or more of the following applies: the molecular mass is around 7000; nitrogen content is above 14%; phosphorus content is above 8.5%; DNA content is less than 1%; protein content is negative in accordance with the biuret test. For example, the purified RNA extract contains more than 14.5% by weight of nitrogen and more than 8.5% by weight of phosphorus. The purified RNA extract is preferably substantially free of proteins, DNA, and nucleotides, for example, at least 95% by weight, preferably at least 99%, pure. The molecular mass can be determined by electrophoresis studies of small RNA in 15% polyacrylamide gel (PAAG), containing DS-Na and 7M urea. (Mette M. F., Autsatz W., van der Winden J., Matzke M. A., Matzke A. J. M., Transcriptional silencing and promoter methylation triggered by double-stranded, EMBO J., 2000, 19, pp. 5194-5201)

For example, electrophoresis studies of yeast RNA extracts showed substantial difference in the molecular mass (FIG. 15). As can be seen on FIG. 15, in accordance with the molecular mass markers of *E. Coli* τRNA and 25-member oligonucleotide, the highly purified yeast RNA moved as homogenous stripe in the 25-nucleotide zone, while the sodium salt of yeast RNA moved as heterogeneous stripe starting from the marker of TRNA with the molecular mass of 19000 and all the way to the stripe of the 25-member oligonucleotide with the molecular mass of 7000. This shows that a highly purified yeast RNA preparation is quite homogenous in accordance with the molecular mass and contains mostly or even essentially 25±10 nucleotides.

A method for purifying total yeast RNA can be used as described in U.S. Pat. No. 6,737,271, the content of which is incorporated by reference herein in its entirety. (Tkachuk Z., Compound, composition and method for the treatment of inflammatory and inflammatory-related disorders. U.S. Pat. No. 6,737,271, May 18, 2004)

The purified RNA extract may be further modified to obtain the RNA-based composition for prophylactic or therapeutic use. Thus, in a composition used as a RNA-based drug that has an advantageous use as antiviral agent according to the invention, the amount of the purified RNA extract in the composition ready for administration is at least about 50% by weight, preferably from about 60 to about 80%, more preferably from about 65% to about 75%, even more preferably at least about 70%.

In a particular aspect of the invention, the composition also contains a sugar, and a proportion RNA extract-sugar in the composition is preferably from about 1.5:1 to about 3.5:1 by weight, more preferably from about 2:1 to about 3:1, even more preferably about 2.5:1. Thus, exemplary RNA-M has mannitol in the proportion RNA: mannitol 2.5:1, i.e., this drug contains at least 70% RNA. Other sugars, for example lactose for RNA-L, can be used instead of or in addition to mannitol, so that the total amount of sugars is in the proportions as above.

For example, regarding RNA-arginine (and/or lysine, histidine, sperimin, spermidine, guanidine), the proportion RNA extract—alkaline organic compounds in the composition is advantageously about 1:1 to about 2:1 by weight, more preferably from about 2.5:2 to about 3.5:2, even more preferably about 3:2. Thus, an exemplary RNA-A has the proportion RNA:arginine 3:2. Other alkaline aminoacids lysine and histidine, as well as spermin, spermidine, and guanidine can be used in the same proportions.

In another aspect of the invention, the RNA extract and sugar-containing composition is obtained by heating the RNA extract with at least one sugar, such as mannitol.

The heating temperature is, for example, in the range from about 40 to about 70° C., and advantageously about 50 to about 70° C., even more preferably about 55 to about 65° C., for example, about 60° C.

Thus, to obtain the exemplary composition based on RNA-M, a solution of yeast RNA:mannitol in the proportion 2, 5:1 is prepared, dissolved in water, warmed up to the temperature 60-65° C., and kept for 10 min. Then the solution is cooled down to the room temperature and dried in vacuum. The dried compound is used for antivirus studies as described below.

Additional substances in the composition can be selected from sugars, mannitol, lactose, alkaline aminoacids such as arginine, lisin, histidine, and aliphatic polylmide such as guanidine, spermin, and spermidine. For example, the RNA extract is treated with alkaline amino acids, such as arginine.

Various pharmacologically acceptable fillers, bearers, carriers, diluents may be used in the composition ready for administration.

Example 1.2. Modification and Choice of RNA with Antiviral Activity

It is known that majority of anti-influenza drugs, such as Tamiflu and others, contain only anti-neuraminidase activity and do not act on the hemagglutinin receptors. Therefore, we decided to select first the drugs with anti-hemagglutinin activity. The reaction of hemagglutination was held in parallel with 1% of chicken erythrocytes or 0.75% of Guinea pig erythrocytes in accordance with the common methodology. (Guidelines for laboratory diagnosis of viral and rickettsial diseases, Moscow, Medicine, 1965, p. 136) The anti-hemagglutinin activity of the resulting yeast RNA from the purification process, and its salts arginine RNA and sodium RNA, in the concentrations 1% and 3%. As indicated by the experiment results presented in Table 1.2.1. below, yeast RNA and its sodium salt do not have anti-hemagglutinin activity, while the arginine salt of yeast RNA, especially in the concentration 1%, possesses substantial anti-hemagglutinin properties.

TABLE 1.2.1

The influence of RNA preparations on the activity of hemagglutinin of influenza virus AFM 1/47 ($H_1N_1$)

| Preparation | Concentration of preparation, % | Virus titer in the experiment, $lg2^x$ | Difference between the experimental and control data, $log\ 2^x$ |
|---|---|---|---|
| Yeast RNA | 3 | 7 | 1 |
|  | 1 | 8 | 0 |
| Arginine yeast RNA | 3 | 5 | 3 |
| RNA-A | 1 | 4 | 4 |
| Sodium yeast RNA | 1 | 7 | 1 |
| RNA-N | 3 | 8 | 0 |
| Control virus |  | 8 | — |

In a second step, we studied complex preparations of yeast RNA with sugars, such as mannitol (M) and lactose, which are commonly used in the production of medical substances as additional substances. For the preparation of a combined compound of yeast RNA and mannitol, we studied the influence of temperature on their solution through their anti-hemagglutinin activity. The water solution of yeast RNA and mannitol was prepared in the mass correspondence 2.5:1; the solution was then held at 10 minutes accordingly at 50, 60, 70, 80 and 90° C., and also at room temperature. Then the solution of RNA and mannitol was cooled down to the room temperature, dried, and studied for the influence of the obtained preparation of RNA-M in the concentration 0.5 mg/ml on the hemagglutinin activity of influenza virus AFM 1/47 $H_1N_1$. The original solution of yeast RNA and mannitol was used for control. Results of the experiment are presented in Table 1.2.2. below.

TABLE 1.2.2

The influence of the temperature of reaction on the hemagglutinin activity of influenza AFM 1/47 $H_1N_1$ virus

| Preparation | Tempreture of reaction, ° C. | Virus titer in the experiment, log2x | Difference in the virus titers, log2x |
|---|---|---|---|
| RNA | 30 | 7 | 1 |
| Mannitol | 30 | 8 | 0 |
| RNA + Mannitol | 40 | 6 | 2 |

TABLE 1.2.2-continued

The influence of the temperature of reaction on the hemagglutinin activity of influenza AFM 1/47 $H_1N_1$ virus

| Preparation | Tempreture of reaction, ° C. | Virus titer in the experiment, log2x | Difference in the virus titers, log2x |
|---|---|---|---|
| RNA + Mannitol | 50 | 5 | 3 |
| RNA + Mannitol | 60 | 4 | 4 |
| RNA + Mannitol | 70 | 5 | 3 |
| RNA + Mannitol | 80 | 6 | 2 |
| RNA + Mannitol | 90 | 7 | 1 |
| Control virus |  | 8 | — |

As shown in the experiment, the combined preparations RNA-M obtained by heating 60±10° C., substantially decrease the activity of hemagglutinin of influenza virus.

The best anti-hemagglutinin activity was demonstrated by the preparation obtained by heating the RNA solution solution of RNA and mannitol at 60° C. Further on, we studied the antivirus activity of the obtained at optimum temperature preparation, which we indicated as RNA-M.

It was assumable that other sugars combined with yeast RNA would also stimulate its anti-hemagglutinin activity. A comparative analysis of anti-hemagglutinin activity of RNA-M with the preparation of yeast RNA, which used lactose as a sugar (RNA-L), prepared at temperature 60° C. as described above for the preparation RNA-M. The results of the comparative analysis are presented in Table 1.2.3. below.

TABLE 1.2.3

The influence of RNA-M and RNA-L in the concentration 10 mg/ml on the hemagglutinin activity of influenza virus AFM $_{1/47}$ $H_1N_1$

| Preparation | Virus titer in control, $lg2^X$ | Virus titer in the experiment, $lg2^X$ | Difference in virus titers, $lg2^X$ |
|---|---|---|---|
| Control virus | 9 | — | — |
| RNA-M | 9 | 5 | 4 |
| RNA-L | 9 | 7 | 2 |

As one can see from the experiment results, the yeast RNA preparation with mannitol, which was treated with temperature, has the highest anti-hemagglutinin activity with regard to the virus AFM 1/47 $H_1N_1$. At the same time, we studied other polyribonucleotides and their anti-hemagglutinin activity. As presented in the test results in Table 1.2.4. below, only the preparation Poly I had distinct anti-hemagglutinin activity with regard to the influenza virus AFM. 1/47 $H_1N_1$.

TABLE 1.2.4

The influence of polyribonucleotide preparations in the concentration 10 mg/ml on the hemagglutinin activity of influenza virus AFM $_{1/47}$ $H_1N_1$

| Preparation | Virus titer in control, $lg2^X$ | Virus titer in the experiment, $lg2^X$ | The difference in virus titers, $lg2^X$ |
|---|---|---|---|
| Poly A Polyadenylic acid | 9 | 7 | 2 |
| Poly C Polycytydilic acid | 9 | 7 | 2 |
| Poly I Polyinosylic acid | 9 | 6 | 3 |
| Poly G Poliguanylic acid | 9 | 9 | 0 |
| Poly U Polyurydylic acid | 9 | 9 | 2 |
| PolyIC Polyinosinic:polycytidylic acid | 9 | 9 | 3 |
| Control virus | 9 | 9 | — |

Compounds Poly, C, 1, G, and Poly Isere obtained from Scientific-Production Association <<Vector>> Berdyanks, Russian Federation.

As Table 1.2.4. above shows, polyribonucleotide preparations had low anti-hemagglutinin activity. Only double-stranded Polyinosinic:polycytidylic acid and single-chain Polyinosylic acid showed significant anti-hemagglutinin activity, but it was lower than RNA-M.

As RNA-M obtained at temperatures of 55-65° C. showed maximum anti-hemagglutinin activity therefore it was used for further research antiviral activity in models in vitro and in vivo.

Hence, the complex preparation of yeast RNA and mannitol (RNA-M) obtained showed the maximum anti-hemagglutinin activity. Consequently, it was used for further anti-virus studies.

Example 2

Summary of Experimental Models and Results

Example 2.1. Models of Influenza Viruses

Example 2.1.1. In Vitro Model of Influenza Viruses

Compounds. The compound under examination—RNA-M. Tamiflu-Oseltamivir by Rochen (75 mg per capsule). Poly (I):Poly(C)— the etalon inductor interferon by Calbiochem. Neuraminidase-neuraminidase compound with *Astrobacter ureafaciens* 1 unit Calbiochern.

Viruses. Influenza virus for experiments in vitro: A/FM/1/47(H1N1), infection titer in MDCK –3.0-7.0 lg $ID_{50}$. Influenza virus for experiments in vivo: A/FM/1/47(H1N1), adapted for lungs of white mice, which had 15 passages on mice, infections titer—4.0 $lgLD_{50}$; 100% of lethality in mice within 5 days. Virus of vesicular stomatitis, Indiana strain, obtained from the virus museum of the Ivanovsky Institute of Virology of the Russian Academy of Medical Sciences (Moscow). The infection titer in cell culture L41 constituted 4.0-5.0 lg $TCD_{50}$ Cell culture. MDCK—consequently re-grafted cell culture of dog kidney, culture environment: RPMI-1640+10 fetal calf serum+antibiotics. L41—lymphoblastic human cells. OH-1—lymphoblastic mice cells.

Determination of the maximum endurance concentration of drugs (MEC) and minimum active concentration (MAC). MEC is the highest dose, which did not cause cell degeneration; MAC—the minimum quantity of drug, which inhibits the development of virus-specific cytopathogenic action (CPA) by 50%. The chemotherapeutic index (CTI) of the drug with regard to influenza virus was discovered by determining the ratio of MEC to MAC. The absence of CPA in the experiment, while CPA being present in the control virus, as well as the difference in the infection titer in experiment compared to the control influenza virus, allowed to calculate drug's MAC. The anti-influenzal activity of the drug in vitro was studied on the consequently re-grafted cell culture MDCK (dog kidney cells) with a solid layer. MEC of RNA-M, we calculated, constituted 5000 microgram/ml; MAC—31 microgram/ml, CTI—161. These indicators, MEC, MAC, and CTI allow categorizing RNA-M as a highly active compound.

When testing the anti-influenzal activity of RNA-M compound in vitro, its preventive and treatment actions were considered. In accordance with the obtained evidence reported in Table 2.1.1. below, RNA-M was effective in the doses 1.25-10 mg/ml in preventive regimen and 0.6-10 mg/ml in treatment regimen.

TABLE 2.1.1

The anti-influenzal action of RNA-M compound in vitro

| Compound concentration, mg/ml | Influence | | | |
|---|---|---|---|---|
| | Preventive | | Treatment | |
| | Infection virus Titer, $lgID_{50}$ | Inhibition indicator, $lgID_{50}$ | Infection virus titer, lg $ID_{50}$ | Inhibition indicator, $lgID_{50}$ |
| 10 | 2.0 ± 0.3 | 5.0 ± 0.75 | 0 | 3.0 ± 0.45 |
| 5 | 2.0 ± 0.3 | 5.0 ± 0.75 | 0 | 3.0 ± 0.45 |
| 2.5 | 0 | 7.0 ± 1.05 | 0 | 3.0 ± 0.45 |
| 1.25 | 0 | 7.0 ± 1.05 | 0 | 3.0 ± 0.45 |
| 0.6 | 7.0 ± 1.05 | 0 | 0 | 3.0 ± 0.45 |
| Control virus | 7.0 ± 1.05 | — | 3.0 ± 0.45 | — |

*$P < 0.05$.

Example 2.1.2. In Vitro Model of Influenza Viruses H1N1 and H5N2

Viruses and cells. MDCK cells were cultivated in Costar® (USA) 96-well plates till a monolayer was reached. The medium used was MEM with the addition of 100 mcg/ml of gentamicin, 5% fetal bovine serum for cell growth, and 1 mcg/ml of trypsin for viral maintainance and cultivation. Influenza viruses A/California/7/09 (H1N1) and A/mallard/Pennsylvania/10218/84 (H5N2) were obtained from the collection of viruses of Influenza Scientific Research Institute of the Russian Medical Academy of Sciences and passaged in the allantoic cavity of 10-12-day-old chicken embryos for 48 hours at 37° C.

Evaluation of drug cytotoxicity. To establish the study drug concentrations, the product toxicity was studied on a MDCK cell line. Drug dilutions (5000-160 mcg/ml) were added to cells and incubated for 48 hours in the same conditions. Thereafter, the cells were washed twice for 5 min. in a phosphate buffered saline. The number of living cells was assessed with a microtetrazolium test (MTT), characterizing the intensity of mitochondrial respiration (1). This was performed by adding into the wells of 100 mcl (5 мг/мл) of 3-(4,5-dimethylthiazolil-2) 2,5-diphenyl tetrazolium bromide (ICN Biochemicals Inc., Aurora, Ohio) dissolved in normal saline solution. The cells were incubated at 37° C. in 5% $CO_2$ air for 2 hours and washed for 5 min. in a phosphate buffered saline. The sediment was dissolved in 100 mcl per well of dimethyl sulfoxide (DMSO); thereafter the optical density in the wells was measured in a multifunctional microplate reader Victor 1420 (Perkin Elmer, Finland) at 535 nm wavelength. The test results for each product permitted to establish a 50% cytotoxic dose ($CTD_{50}$), i.e., drug concentration causing death of 50 percent of culture cells.

Evaluation of antiviral drug action. The cell culture was infected 1 hour after contact with RNA-M. Different serial tenfold dilutions of the study drug ranging from $10^{-1}$ до $10^{-7}$ were introduced into well plates with MDCK cell culture. Subsequently, the cells were incubated in a thermostat for 48 hours at 37° C. The virus-infected cell culture was used as a positive control, and an intact cell culture (into which a maintenance medium was introduced instead of a study drug) served as a negative control. The results were assessed 48 hours after incubation. The virus infectious titer was assessed in well plates for immunological assays into which the culture fluid was transferred. Equal volumes of 1% chicken red blood cells were added. The presence of the virus was assessed by evaluation of hemagglutination in the study and control wells. The hemagglutination titer of virus was defined as the reciprocal of the highest log virus dilution that hemagglutinated chicken red blood cells. The antiviral activity was assessed by evaluation of decrease of infectious titer as compared with control. The obtained data permitted to estimate the drug median effective dose ($ED_{50}$), i.e., drug concentration permitting to achieve a twofold decrease of viral activity as compared with control, and selectivity index defined as a ratio of $CTD_{50}$ to $ED_{50}$, characterizing selectivity of virus-inhibiting drug action as compared with cells. (Mosmann T., Rapid colorimetric assay for cellular growth and survival: application to proliferation and cytotoxicity assays, J. Immunol. Methods, 1983, 65, pp. 55-63)

The study results have shown that cytotoxic dose of RNA-M was exceeding 5000 mcg/ml. In cases of influenza A/California/7/09 (H1N1) virus the effective dose ($EC_{50}$) of RNA-M was equal to 500 mcg/ml, and its selectivity index was >10. In cases of avian influenza virus A/mallard/Pennsylvania/10218/84 (H5N2) the drug is effective at higher concentrations ($EC_{50}$=1519 mcg/ml), and its selectivity index is >3.

Example 2.1.3. In Vivo Model of Influenza Viruses

The anti-influenzal activity of RNA-M in vivo was studied on the model of influenza pneumonia in mice, both in preventive and treatment regimens. The compound solution was introduced to non-inbreeding mice intravenously or intranasally 24 hours prior to intranasal infection with the influenza virus, adapted to lung culture of mice, in the doses of 10 $LD_{50}$ (preventive regimen) and 24 hours after infection with the influenza virus (treatment regimen). At the same time a control group with influenza virus was formed for the preventive and treatment regimens. The effectiveness of the drug was tested by the index of effectiveness of inhibition of lethality and influenza infection titer in mice lung culture.

Determination of interferon activity was done in accordance with the generally used methodology of inhibition of CPA vesicular stomatitis virus in cell culture OH-1.

Calculation of neuraminidase activity was done in accordance with the methodology by D. Aminoff. (Amminoff D., Methods for the quantitative estimation of N-acetyl-neuraminic acid and their application to hydrolysates of sialomucoids, Biochem. J., 1961, 81, pp. 384-392) The hemagglutination reaction was carried out in parallel with 1% of chicken erythrocytes or 0.75% erythrocytes of Guinea pig in accordance with the generally accepted methodology The infection titer of influenza virus was determined by presence of hemagglutination of the virus. (Guide to laboratory diagnosis of viral and ricketsia diseases, Moscow Medecine, 1965, p. 136)

The studies on anti-influenzal activity of RNA-M in vivo were carried out with different methods of introduction in both preventive and treatment regimens as shown in Table 2.1.2. below.

TABLE 2.1.2

Anti-influenzal action of RNA-M in vivo in preventive and treatment introductions

| Dose mg/kg | Way of introduction | % died | CP (Coefficient of protection) | IE (Index of effectiveness) |
|---|---|---|---|---|
| Preventive regimen | | | | |
| 1500 | Intranasal | 80 ± 1.25 | 1.25 | 25.0 |
| 1000 | Same | 33.3 ± 1.67 | 3.0 | 66.6 |
| 500 | " | 80 ± 1.25 | 1.25 | 25.0 |
| 50 | " | 100 | 1.0 | 0 |
| 15 | " | 66.6 ± 3.33 | 1.25 | 25.0 |
| 150 | Intra-abdominal | 60 ± 3.0 | 1.7 | 41.2 |
| 50 | Same | 60 ± 3.0 | 1.7 | 41.2 |
| 15 | " | 60 ± 3.0 | 1.7 | 41.2 |

TABLE 2.1.2-continued

Anti-influenzal action of RNA-M in vivo in preventive and treatment introductions

| Dose mg/kg | Way of introduction | % died | CP (Coefficient of protection) | IE (Index of effectiveness) |
|---|---|---|---|---|
| 150 | Intravenous | 60 ± 3.0 | 1.7 | 41.2 |
| 15 | " | 80 ± 1.25 | 1.25 | 25.0 |
| Tamiflu | Intra-abdominal | 30 ± 1.0 | 5.0 | 70.0 |
| Control virus | | 100 | 1 | 0 |
| Preventive regimen | | | | |
| 1500 | Intranasal | 80 ± 1.25 | 1.25 | 25.0 |
| 1000 | Same | 100 | 1.0 | 0 |
| 500 | " | 60 ± 3.0 | 1.7 | 41.2 |
| 50 | " | 40 ± 2.0 | 2.5 | 60.0 |
| 15 | " | 44.4 ± 2.2 | 2.25 | 52.0 |
| 150 | Intra-abdominal | 40 ± 2.0 | 2.5 | 60.0 |
| 50 | Same | 60 ± 3.0 | 1.7 | 41.2 |
| 25 | " | 40 ± 2.0 | 2.5 | 60.0 |
| 15 | " | 100 | 1.0 | 0 |
| 150 | Intravenous | 100 | 1.0 | 0 |
| 15 | Same | 20 ± 1.0 | 1.25 | 20.0 |
| Tamiflu | Intra-abdominal | 20.0 ± 0.5 | 10.0 | 80.0 |
| Control virus | | 100 | 1.0 | 0 |

In preventive regimen, the effective dose in case of intra-abdominal and intravenous introduction constituted, and 15, 50, 150 mg/kg; in case of intranasal introduction, it was considerably higher-1000 mg/kg. In treatment regimen, the compound was effective in case of intra-abdominal introduction and for intranasal introduction in lower doses, respectively 25 mg/kg (IE=60.0) and 50 mg/kg (IE=60.0).

When studying the mechanism of action of RNA-M, neuraminidase, hemagglutination and interferonegenic activity was considered. The experiments on the influence of RNA-M on the hemagglutination activity of A/FM/1/47 (H1N1) influenza virus were held using the doses of the compound 1.0; 3.0; 10.0; 30.0; mg/ml. In accordance with the results, RNA-M in the doses 1.0; 3.0; 10.0 mg/ml statistical reliably (by 4 times) decreases hemagglutination activity of influenza virus hemagglutinin: the titer in the mentioned doses constituted 16±2.4, while the control titer was 64±9.6.

The neuraminidase activity of RNA-M was studied on the example of influenza virus neuraminidase with RNA-M 1.0; 3.0; 10.0; 30.0 mg/ml (the contact with the compound lasted for 1 and 18 hours). The results of the experiment reported in Table 2.1:3. below demonstrated, that in case of action of the compound in the doses of 10 and 30.0 mg/ml during 1 hour, the inhibition of neuraminidase activity of influenza virus was total for 100%, in the doses of 1 and 3 mg/ml—for 50%.

TABLE 2.1.3

Inhibition of neuraminidase activity by RNA-M

| | | Inhibition of neuraminidase activity, % | | | |
|---|---|---|---|---|---|
| | | Contact with the compound for 1 hour | | Contact with the compound for 18 hours | |
| Drug | Dose, mg/kg | UA/549 | % of inhibition | UA/549 | % of inhibition |
| RNA-M | 30 | 0.085 ± 0.012 | 100 | 0.070 ± 0.008 | 100 |
| | | 0.092 ± 0.014 | 100 | 0.065 ± 0.0078 | 100 |

TABLE 2.1.3-continued

Inhibition of neuraminidase activity by RNA-M

Inhibition of neuraminidase activity, %

| Drug | Dose, mg/kg | Contact with the compound for 1 hour | | Contact with the compound for 18 hours | |
|---|---|---|---|---|---|
| | | UA/549 | % of inhibition | UA/549 | % of inhibition |
| | 10 | 0.080 ± 0.012 | 100 | 0.080 ± 0.009 | 100 |
| | | 0.087 ± 0.013 | 100 | 0.078 ± 0.009 | 100 |
| | 3 | 0.420 ± 0.06 | 50 | 0.075 ± 0.008 | 100 |
| | | 0.417 ± 0.063 | 50 | 0.072 ± 0.072 | 100 |
| | 1 | 0.430 ± 0.065 | 50 | 0.440 ± 0.05 | 50 |
| | | 0.435 ± 0.065 | 50 | 0.410 ± 0.05 | 50 |
| Control virus | | 0.950 ± 0.14 | | 0.910 ± 0.11 | |
| | | 0.920 ± 0.138 | | 0.890 ± 0.11 | |
| Control fetuine | | 0.059 ± 0.009 | | 0.070 ± 0.01 | |
| | | 0.072 ± 0.011 | | 0.063 ± 0.007 | |

In case of the longer contact (18 hours), the total inhibition of neuraminidase of influenza virus was recorded in case of action of the compound in the doses 3.0; 10 and 30.0 mg/ml and 50%—in the dose of 1 mg/ml. Therefore, RNA-M in doses 1.0; 3.0; 10.0 and 30.0 mg/ml inactivates influenza virus neuraminidase by 50 and 100%; in doses 1.0; 10.0 and 30.0 mg/ml statistical reliably decreases its hemagglutination activity.

Testing of interferon induction by RNA-M compound in experiment in vivo was carried out on mice, which were introduced with 50 mg/kg of the drug intra-abdominally. After 1, 2, 3, and 6 days, the presence of interferon in blood serum of the animals was tested in accordance with the general methodology of inhibition of CPA of vesicular stomatitis in consequently re-grafted cell culture of mice OH-1 (lymphoblastic mice cells).

The dynamics of interferon induction by RNA-M in mice demonstrated that the maximum activity of interferon was registered on the first day, later decreasing twice and remaining at the same level on the $6^{th}$ day (Table 4). Acid-endurance marker interferon shows that RNA-M-induced interferon is Alpha-interferon.

TABLE 2.1.4

Interferonegenic activity of RNA-M in vivo

| Time of testing, day | Interferon titer, units of activity | |
|---|---|---|
| | −pH | +pH |
| 1 | 160 ± 19.2 | 160 ± 19.2 |
| 2 | 80 ± 9.6 | 80 ± 9.6 |
| 3 | 80 ± 9.6 | 40 ± 4.8 |
| 6 | 80 ± 9.6 | 80 ± 9.6 |

While analyzing the obtained results, it is necessary to note that the mechanism of anti-influenzal action of RNA-M is carried out due to the influence on the activity of neuraminidase and hemagglutinin and induction of alpha-interferon.

Example 2.1.4. Treatment of Influenza and ARVD in Human Patients

Clinical trial was pursued as open, randomized, comparative, parallel. This trial was planned as superiority trial. 170 patients were included in this study and, using a simple randomization method, were divided into the test group (85 patients) and the control group (85 patients). Men and women of 18 to 70 years of age with diagnosis acute respiratory viral infection (ARVI) or influenza took part in the study. The main criteria for patient to be taken into the trial were: virus presence, (positive immunofluorescent test); body temperature≧38° C., which was accompanied by fever and pain syndrome; subjective complains (asthenia, mialgia, headache, sore throat and\or cough. As a comparative antiviral medication in contrast to RNA-M, Tamiflu was used. Moreover, patients were treated according the standard protocol for nosology. Medication RNA-M was firstly put on 0.5 grams 3 times per day for 5-7 days, and than till the $14^{th}$ day inclusively 0.25 grams twice a day. Tamiflu was prescribed according to the instruction.

Analysis of the treatment efficacy in each of the groups was estimated using the primary variables: headache, asthenia, catarrhal signs (cough), body temperature (less than 37° C.). As secondary variables in this trial were taken: fever, sore throat, joint pain, mialgia, fatiguability, nasal discharge, pruritus and burn in the nasal ducts, catarrhal signs (cough, rhinitis etc), intensity of which was estimated according to verbal analog scale (0-3 points). Study included immunological examination, which was conducted with monoclonal antibodies. Influenza virus was identified by means of identification of mRNA of Influenza virus A and Influenza virus B. In case of positive results for Influenza virus A, additional PCR analysis for Influenza virus A/H1/N1 was done on Rotor-Gene 6000 amplificator. Diagnosis influenza and ARVI was confirmed by means of immunofluorescent express-method (MFA) and serologically (HIR). With that influenza virus A was detected in 32.94% of patients, influenza virus B—in 8.24% of patients, parainfluenza virus—in 41.18% of patients, adenoviral infection—in 8.24% of patients, respiratory-syncytial infection—in 9.41% of patients.

Statistical methods. Data analysis was done using built-in modules for statistical analysis Microsoft Excel and program SPSS 13.0. For data analysis were used methods of descriptive statistics (for the quantity variables were calculated—n, mean, median, standard deviation, minimum, maximum, and for categorical variables—count and percentage), graphical methods, methods of confidence interval estimation (estimation of 95% CI for means and medians depending on the normality of data distribution), methods of two-factor ANOVA using mixed model with the further usage of simple contrasts. Mann-Whitney test or Student test for independent samples (depending on the normality of data distribution) was used for determination of difference relevance between two groups, Wilcoxon signed-rank test or Student test for paired data was used to compare data before and after the treatment. Normality of data was checked by Shapiro-Willes test. Confidence interval for two medians difference was calculated by Hodges-Lehmann method. For Shapiro-Wilk's test we took significance level equal to 0.01, for all other tests 0.05.

Effectiveness analysis on the basis of disease symptoms variables. Intensity of disease symptoms variables was measured according to VAS (verbal analog scale), which included the following rank-ordered categories, which were equivalent to the number of points: 0 points—no signs, 1 point—mild, 2—moderate, 3—severe.

Graphically the dynamics of the mean values of subjective complains and objective symptoms of the disease are shown in FIG. 1-FIG. 10.

A decrease in symptoms intensity (high body temperature, fever, headache, sore throat, joint pain, myalgia, itch and burn in the nose, tiredness, general weakness and catarrhal signs) in the main group as compared to the initial conditions (day 0) were statistically significant starting on day 4.

FIGS. 1-4 show graphically the dynamics of the main symptoms of the disease: high body temperature, headache, catarrhal signs and general weakness. Shown on the mentioned graphs curves are similar and differences between the groups according to differences (day i-day 0) in all the variables are statistically significant starting from the day 4. This indicates that the decrease in the symptoms intensity in the main group is much bigger already on the $4^{th}$ day as compared to the control group. Such decrease remains to be significant for such variables as "high body temperature" till the day 14 (FIG. 1), headache" till the day 10 (FIG. 2), catarrhal signs till the day 6 (FIG. 3), and also day 21, and in the "general weakness" variable this decrease remains significant till the day 6. Such a result means that the decrease in main symptoms intensity in the main group comes much earlier (on the $4^{th}$ day) as compared to the control group; and this difference in two variables remains significant till day 14 and day 21 inclusive.

Obtained results indicate that the decrease in symptoms intensity in the main group are much bigger and it occurs earlier as compared with the control group, and this decrease mainly for 2-3 days remains considerable till the end of the treatment.

Basing on the data, shown in FIGS. 1-10 it could be stated that there was seen a tendency to a faster decrease in symptoms intensity in the main group than in the control one.

In order to evaluate intensity of symptoms in each of the groups was done DA according to a mixed model:—dependent variable—symptom criteria, which is being analyzed, "time" factor—fixed (levels: day 0, day 2, day 4, day 6, day 8, day 10, day 10, day 14 and day 21), "patients" factor—random. For those dependent variables, which were not in agreement with ANOVA (residuals distribution normality), was used ANOVA on ranks.

According to ANOVA results, effect of the "time" factor is significant, which points to a positive influence of treatment on the decrease in symptoms intensity so in the main, as in the control groups.

Analysis of treatment efficacy in subgroups infected with different viruses. Additionally was conducted a comparative analysis between the test and the control groups in patients subgroups, infected with different viruses, according to the following primary variables:

time of temperature normalization
time of headache relief
time of the general weakness relief Since the data, which were analyzed, did not correlate with the Gaussian distribution, as a measure of the central tendency for all the variables we took median, values of which are shown in comparative diagrams (FIGS. 11-14).

Done using Mann-Whitney test comparison of the correspondent subgroups of the test and the control groups enabled to state that there are statistically significant changes between the test and the control groups on the basis of the primary variables and to conclude that there is a tendency in mean values to decrease in the main group as compared to the control one.

Thus, it could be stated that the therapy effectivity in the test group, which included RNA-M, was higher than the effectivity of Only the conventional therapy on the basis of the mentioned variables (time of temperature normalization, time of headache relief, time of the general weakness relief).

Results of our trial indicate that independently of the virus (infuenza or parainfluenza, adenoviral infection), which comprises 80% of patients, medication essentially shortens the time of the decay of the main ARVI symptoms.

Example 2.2. Models of Hepatitis C virus

Studies on the activity of new drugs require an experimental model for the HCV infection. However, for a long time, it had been difficult to create, since the levels of HCV replication in viiro systems had been low and possible to register only by the PCR method. (Deryabin P. G., Isaev E. I., Vyazov S. O. et al., Vopr.vyrusol, 1997, 6, pp. 251-253) The standard models used by authors are MT-4 cells, Daudi cells, as we as, Hela cells, transformed recombinant plasmid (pBK-CMC-HCV—replikon) which contain structural genes of HCV and transfected cells of human hematoma—Huh-7, by lyutsefiraza reporter constructs pGL3. (Helbig K. J., George J., Beard M. R., A novel I-TAC promoter polymorphic variant is functional in the presence of replicating HCV genotype, J. Clin. Virol., 2005, 32, 2, pp. 137-143) Recently achieved successful extraction from the blood senim of infected people of a cytopathogenic version of HCV, able to aggregate in high titer in cell cultures of different origin, allowed the search for new models for studies and treatment of the HCV infection. (Deriabin P. G., Lvov D. K., Isaeva E. I., Biological properties of citopathogenic hepatitis C variants, 21st International Congress of Virology, Sydney, 1999, 13, p. 2)

For the extraction and culturing of HCV, the authors used the experimental models re-grafted cell cultures of human adenocarcinoma of adrenal gland SW-13, re-grafted culture of the cells of lymphoblastic origin—MT-4, original cell cultures of newborn mice brain. (Helbig K. J., George J., Beard M. R., A novel I-TAC promoter polymorphic variant is functional in the presence of replicating HCV genotype., J. Clin. Virol., 2005, 32, 2, pp. 137-143) Identification of the cytopathogenic effect of the virus was held on the cultures permissive to reproduction of Flaviviruses: re-grafted line of kidney cells of pig embryo, re-grafted line of pig testicular cells. The obtained virus had high infection and anti-gene qualities, effectively neutralized by HCV-specific antibodies.

With the help of neutralizing reactions, inhibiting of hemagglutination by specific antibodies, immunoenzyme method, immunofluorescence method and reaction of diffusion precipitation in agar, the cytopathogenic isolate of HCV was identified. The RNA of this virus version was identified as HCV genome in PCR with the use of 5'-NTR primers on the HCV genome area responsible for codification of nucleocapsid protein, as well as with the method of sequencing of the HCV genome fragment responsible for the codification of nucleocapsid protein of HCV. The authors (Venison L. V., Sobolev B. N., Tissue tropism of hepatitis virus C, Viral hepatitis: Prospects and achievements, 1999, 12, pp. 11-17; Deriabin P. G., Lvov D. K., Isaeva E. I., Biological properties of citopathogenic hepatitis C variants, 21st International Congress of Virology, Sydney, 1999, 13, p. 2) presented the proof of extraction of HCV, modeling of productive and persistent infection in vitro. However, HCV extracted by the authors has not been registered yet in the International collection and is not standard.

Example 2.2.1. Model of Suspension Culture MT-4 Infected with HCV

In the experiments, the re-grafted suspension culture MT-4 of lymphoblastoid origin, which was cultured on the nutrient medium RPMI-1640 with a 10%-solution of fetal serum and antibiotics, was used. As the source of HCV, an undiluted blood serum of patients with HCV, which had HCV RNA with different virus load, was used as shown in Table 2.2.1. below.

TABLE 2.2.1

Human serums containing HCV

| Serum No. | Genotype | Resulting virus load, g/eqv. |
|---|---|---|
| 1 | 2 | 10-100 thds. |
| 2 | 1b | 100 thds.-1 Mio. |
| 3 | 3a | 1-10 Mio. |

It is known that splitting of structural proteins in HCV is done by the cell peptidases and virus protease. Therefore, for successful culturing of HCV in the test cultures, the method of preliminary treatment of the cells with TPCK-tripsin of XIII-type from the pancreas of calf (Sigma, USA) was used. For this purpose, the mono-layer was washed three times in 6 ml of the medium DMEM containing 2 mcl/ml of TPCK-tripsin. Tripsin-treated cells were inoculated by undiluted sterile blood from HCV-infected patients in the amount 0.2 nm. 30 minutes past the contact, the monolayer of cells was washed twice with the purpose of removing the unabsorbed virus, and embedded with the nutrient medium RPMI-1640 with 2% fetal serum and antibiotics. The infected cells had been incubated at 36.5° C. for 7 days.

On the 5$^{th}$ day, the virus in cell culture was tested by the PCR method with the use of Amplisense kit. (Boom R. C., Sol J. A., Salimans M. M. M., Jansen C. L., Wertheim-van Dillen P. M. E., van der Noordaa J., Rapid and simple methods for purification of nucleic acids, Journal of Clinical Microbiology, 1990, 28, 3, pp. 495-503) with modifications (Carter M. J. and Milton I. D., An inexpensive and simple method for DNA purification on silica particles, Nucleic Acids Research, 1993, 21, p. 1044)

For the quantitative assessment of virus load, the method of amplified DNA titration was used. Infection virus titer of HCV was determined on the 5$^{th}$ day of infecting of MT-4 cultures with 10-times-delluted HCV-solution. Infecting of cell culture MT-4 was held with HCV-containing human blood serums. HCV was determined in the cell culture by PCR method on the 5$^{th}$ day of culturing. Depending on the version of serum, the virus load constituted from 1 to 10 and 100 thds g/eqv. In the infected cells MT-4, HCV was determined with high load, hence, the effectiveness of virus release was high.

The stability of culturing in cell culture MT-4 was proved by determination of HCV reproduction in subsequent passages.

Determination of the infection titer of culturing viruses was held with the help of PCR and by calculating virus cytopathic action (CPA) in cell culture. The infection titer of virus was 5.5 lg ID$_{50}$. Anti-HCV inactivated serum completely neutralized virus infectiveness expressed in RNA-HCV to titer 1:640. HCV control constituted—100 thds-1 mio g/eqv.

Studying of antivirus activity of RNA-M on the model of HCV started from the determination of chemotherapeutic index (CTI) of the drug by determination of the correspondence of the maximum tolerance concentration (MTC of RNA-M constituted 50 mg/ml), to the minimum active concentration (MAC), which constitutes the minimum quantity of drug, which inhibits the virus load of HCV by 50%.

For the calculation of MAC in the cell culture MT-4 the test virus was introduced in the dose 100 CCID$_{50}$/0.1 ml and inhibited for 1 hour at 37° C. After the adsorption of virus, the residue on the cells was removed, and the cells were washed by the nutrient medium RPMI-1640. After this, RNA-M in the concentrations 0.125 to 1 mg/ml was introduced to the supporting medium (RPMI-1640 and 2% fetal serum). Virus reproduction was calculated by PCR by genome/equivalent per cell as shown in Table 2.2.2. below.

TABLE 2.2.2

Effectiveness of inhibiting of HCV reproduction by RNA-M

| Drug concentration, mg/ml | Virus load, IU/ml | Virus load, cop/ml | Inhibiting of HCV virus load, % |
|---|---|---|---|
| 1 | 1620 | 6480 | 0 |
| 0.5 | 0 | 0 | 100 |
| 0.25 | 736 | 2944 | 50 |
| 0.125 | 1694 | 6775 | 0 |
| Virus control | 1694 | 6775 | — |

It was demonstrated that the effectiveness of inhibition of HCV reproduction by RNA-M grew from 50 to 100% and depended on the drug concentration correspondingly from 0.25 to 0.5 mg/ml.

The results of studying of RNA-M showed that its maximum tolerance concentration constitutes 50 mg/ml; the minimum active concentration is 0.25 mg/ml, and the chemotherapeutic index was 200. In accordance with these indicators, RNA-M can be classified as a highly active anti-HCV drug.

Example 2.2.2. Model of Culture of Cells Transfected by cDNA of HCV

The experiments were held on MT-4 cell line—interruptive suspension cell culture of lymphoblastic origin. As the source containing HCV, the authors used undiluted blood plasma of patients with HCV, which contained HCV RNA with different virus load.

For the receipt of producing HCV cell cultures, HCV RNA was extracted. 100 mcl of samples—blood serum or plasma of patients with HCV—were introduced to the test-tubes containing 450 mcl of lytic solution and 5 mcl of internal control sample (ICS). 25 mcl of re-suspended sorbent was introduced to each test tube with a separate tip. Sorption was held at the room temperature for 5 min, slurring on vortex. Then the test tubes were velocity sedimented at 10,000 rev/min for 30 sec. on a micro-centrifuge. The supernatants were sucked off with the help of vacuum. 400 mcl of the solution for washing No. 1 was added to the sediment. Then it was mixed on vortex until complete re-suspension of the sorbent and velocity sedimented for 3 sec at 10,000 rev/min. The supernatants were sucked off with the help of vacuum. The sediment was washed twice with the solution for washing No. 3 (500 mcl) with 70% ethanol. The sorbent was re-suspended and sedimented at 10,000 rev/min. The supernatants were sucked off with the help of vacuum. The last washing, analogously to the previous one, was done with acetone (400 mcl) and the supernatants were taken from each test tube. The sediment was dried in the thermostat <<Biokom>> (Russia) at the temperature 60° C. for 10 min. RNA elution was held in 50 mcl of de-ionized water, without ribonuclease and incubated in a thermostat for 3 min at 60° C. The supernatants contained purified RNA. These probes were ready for the reaction of reverse transcription and PCR.

The reaction of reverse transcription was held in accordance with the recommendations of the producer with the help of the reagent kit <<Reverta-L>> (FGUN <<CNIIE>> Rospotrebnadzor, Moscow), which was designated for obtaining cDNA on the RNA matrix of infection agents, for further analysis by the method of PCR. RNA solution extracted with the use of reagent kit <<RYBO-sorb>> ((FGUN <<CNIIE>> Rospotrebnadzor, Moscow) was used as test material. The reaction mix consisted of freeze-dried DTT, 125 mcl of RT-mix solution and 6 mcl of reverse transcriptase (MMLV). 10 mcl of the RNA probe was added to 10 mcl of ready reaction solution. Reverse transcription was held at 37° C. for 30 min, which resulted in the receipt of cDNA.

Transfection of suspension cultures MT-4 was held with the help of calcium-phosphate method. (Deryabin P. G., Lvov D. K, Isaeva E. I., Biological properties of cytopathogenic hepatitis variants, 21st International Congress of Virology, Sydney, 1999, 13, p. 2) For this, the isotonic solution with HEPES buffer, phosphate and DNA was mixed with calcium chloride: the resulting sediment consisted of calcium phosphate particles and DNA. The suspension was added to the cell culture, which absorbed its particles. The solutions A—HEPES—pH 7.1—300 mcl and B—2 M $CaCl_2$—300 mcl were prepared. For the preparation of solution B, 20 mkg of cDNA of HCV was added to 36 mcl of $CaCl_2$ and brought with the distilled water to 300 mcl. Then the solution A was added drop-wise to the solution B, blown through with air and held for 30 min at the room temperature until sedimentation. The sediment was added drop-wise to the cell culture MT-4. The culture of transfixed cDNA HCV was incubated at 34° C. in the thermostat with the inflow of 5% $CO_2$. Testing of the virus in MT-4 cell culture was held by PCR method on the $2^{nd}$ passage on the $9^{th}$ day of culturing, and on the $5^{th}$ passage on the $17^{th}$ day of culturing.

After 30 days of culturing, the cultures of producing cells MT-4, transfected with HCV, were frozen in liquid nitrogen. 24 hours prior to freezing of the cell culture, the nutrient medium (RPMI-1640+10% fetal serum) was replaced with the supporting medium (RPMI-1640+2% fetal serum). Dimethyl sulfoxide (DNSO), which was introduced to the preliminary cooled cell mix, was used for freezing. Then the cells were transferred to the liquid nitrogen. 1 month later, the producing MT-transfected HCV cultures were unfrozen and cultivated in thermostat at the temperature 36.6° C. with the inflow of 5% $CO_2$.

Studies on antivirus activity of RNA-M on the model of producing culture of cells, transfected by cDNA of HCV. Further studying of antivirus activity of RNA-M was held on the model of producing culture of cells transfected by cDNA of HCV. It is known that HCV too badly reproduces itself in cell cultures for the generation of high primary virus concentrations. Therefore, for the experimental studying of these drugs, "surrogate" viruses are used (Dugound D., Fenn J., Siu R. et. al., In vitro characterization of Celgosivir, a clinical stage compound for the treatment of HCV infections, Med. Virol., 2003, 71, pp. 391-398) Surrogate viruses are substitutes for the viruses which can not be reproduced in the necessary quantity in cell culture. As HCV virus surrogate, the bovine viral diarrhea virus (BVDV), which is a test model of HCV. (Dugound D., Siu R., Fenn J. et. al., Synergistic inhibition of flaviridae virus by Celgosivir in combination with Ribavirin or interferon-α, Hepatology, 2002, 36, pp. 1259-1265)

In the course of the studies, we obtained a producing culture of MT-4 cells, transfected by cDNA HCV, which had a stable reproduction of HCV both before freezing of transfixed MT-4 cells and after de-freezing.

MT-4-cDNA cell culture, which contained respective HCV viruses (virus load in the RNA of HCV in the producing culture MT-4-cDNA constituted 12320 g/eqv) and BVDV (infection titer of BVDV in the control was 7.0 lg $ID_{50}$,), was treated with RNA-A in the concentrations 1 and 0.5 mg/ml. The antivirus activity was assessed by infection titer of HCV in PCR and lg $OD_{50}$. The results of studies on antivirus activity of RNA-M on the model MPCC-BVDV, showed that the drug in the concentration 1 mg/ml inhibits the reproduction of viruses by 2.0 lg $ID_{50}$, while in the concentration 0.5 mg/ml accordingly by −3.0 µg $ID_{50}$.

Therefore, RNA-M in the doses 0.5 mg/ml and 1 mg/ml inhibited virus reproduction in all tested systems: surrogate HCV of the bovine viral diarrhea virus, cultured virus and producing culture MT-4-cDNA of HCV.

Example 2.2.3. Treatment of Hepatitis C in Humans

In treatment of human patients with hepatitis C, the "gold standard" of complex therapy—peg-interferon and ribavirin—gives only to 60% efficiency and is expensive. The laboratory efficiency (PCR RNA HCV amount of virus in 1 ml. of serum of blood) of RNA-M at complex treatment of patients with hepatitis C in the stage of replication virus in a group of group (6 person) was studied. Drugs were appointed on a chart: 1th month—RNA-M 3 capsules and 5 capsules of Ribarin "Parmastart" Ukraine (Ribavirin) per day, 2th month—RNA-M 2 capsules per day and 5 capsules Ribarin.

An early virologic answer (2 months after the beginning of treatment) was noticed for all patients. The amount of virus in 1 ml of serum of blood for patients hesitated scope from 1.72×106 to 3.8×106 copies/of ml of RNA HCV (on the average—2.99×106) to beginning of treatment. Control quantitative determination in plasma of blood of RNA HCV for patients showed a decline to the amount of virus in 1.6-3.5 times (on the average in 2.7 times), and are made from 5.6× 105 to 2.3×106 copies/of ml of RNA HCV (on the average 1.28×106) scope.

High efficiency of RNA-M was confirmed for treatment of patients with hepatitis C. The improvement of feel of patients, stabilizing of biochemical indexes, decline of amount of copies of virus, is marked in the serum of blood. RNA-M is tolerated well, side effects were not registered.

Example 2.3. Models of Herpes viruses

Example 2.3.1. In Vitro Models of Herpes Viruses

Drugs. RNA-M is administrated in the dose ranging from 0.1 mg to 1 g per kg of body weight. Virolex® (KRKA, Slovenia), PolyI:PolyC—a standard IFN inductor "Calbichem".

Viruses and cell culture. Herpes simplex virus (HSV-1): a lyophilized antigenic type 1 virus, VC strain was used, obtained from the museum of D. Ivanovsky Virology Institute of the Russian Academy of Medical Sciences. The infectious titer estimated from virus cytopathogenicity in the RK-13 cell culture was 5.0-5.5 lg $CCID_{50}/0.1$ ml, in white mice infected intracerebrally it was 4.0-4.5 lg $LD_{50}/0.03$ ml. Herpes simplex virus (HSV-2), BH strain. The virus was maintained through serial passages in the RK-13 cell culture. The infectious titer estimated from cytopathogenicity in the cell culture was 5.5-6.0 lg $CCID_{50}/0.1$ ml. Before the experimental studies were initiated the virus was stored at minus 70° C. Cell culture. Cells of rat gassserian ganglion neurinoma (NGUK-1) were obtained from rat Gasser ganglion neurinoma induced by transplacental administration of ethylnitrosourea. Reinoculated rabbit kidney cell lines (RK-13) were obtained from the collection of Center for Disease Control (CDC) cell museum (Atlanta, Ga.). The reinoculated lines were cultivated at 37° C.+5% $CO_2$ in a medium consisting of RPMI-1640, 10% fetal calf serum and antibiotics.

Determination of maximum tolerance concentration. Maximum tolerance concentration (MTC) was studied with the use of RK13 and MDCK cells. At least 10 well rows in plates with cell culture for each drug dilution in a culture medium were used in the experiments. Well plates with cell cultures were incubated for 5 days at 37° C. in gas mixture containing 5% $CO_2$. The study and control cell cultures were evaluated daily for the presence or absence of cytopathic action (CPA). The degree of CPA was assessed by cell morphology analysis (rounding, cell shrinkage, and detachment of degenerated cells from well plates) on a 4-point scale. Maximum tolerance concentration (MTC) was defined as the maximum concentration of the drug which was not causing cellular degeneration.

Evaluation of chemotherapeutic index. The chemotherapeutic index (CTI) of the drug with regard to herpes simplex virus (HSV-1) and influenza virus was calculated as the ratio of the MPC to the minimum active concentration (MAC). MAC was defined as the lowest concentration of the drug capable of inhibiting the virus-specific CPA by 50%. For MAC evaluation the test-virus dose of 100 $CCID_{50}/0.1$ ml was introduced into RK13 and MDCK cell cultures and incubated at 37° C. for 1 hour. After viral adsorption on the cells, it was removed and the cells were washed with the medium. Subsequently, RNA-M in a dose of 60 to 1000 mcg/ml was added into the maintenance medium (RPMI-1640+2% fetal serum). The absence of CPA in the experiment (while it was present in the control) as well as the difference of infectious titer in experiment compared with the control permitted to determine the MAC of the drug.

Cytological analysis. Cytological analysis was performed on HSV-sensitive cells cultivated on coverglasses after fixation for 30 min. in the Shabadash fluid. The latter consists of 9 parts of copper nitrate in ethyl alcohol mixed with 1 part of neutral formalin. Standard staining with hematoxiline-eosine was performed. Mitotic index was calculated by counting the number of mitoses in 3,000-10,000 cells and expressed as the number of mitoses per 1,000 cells (‰). Simultaneously, assessment for the presence of pathological mitoses was performed. Pathological mitoses were classified according to Bliumkin classification. (Blumkin V. N., Zhdanov V. M., Effect of viruses on the chromosome apparatus and cell division, M. Medicine, 1973) Cytological specimen were analysed under a x100 and x40 objective and a x10 eyepiece with the use of a Standard 20 Zeiss microscope.

The maximum tolerance concentration of RNA-M as assessed on RK13 cells was found to be 5,000 mcg/ml. The chemotherapeutic index of RNA-M defined as the lowest drug concentration capable of inhibiting the virus-specific CPA by 50% was calculated as the MPC to MPA ratio. RNA-M was studied at concentration range from 60 to 1,000 mcg/ml. The results showed that the inhibiting activity of RNA-M lg $ID_{50}>2$ lies within a concentration range of 60 до 1,000 mcg/ml, its MAC is equal to 60 mcg/ml, its MPC is 5000 mcg/ml, and its chemotherapeutic index is 83.3. According to current guidelines (Guidelines: Pre-clinical drug research, Kyiv, 2001, pp. 371-396), a substance or a drug is considered to have antiviral properties if it is capable of to inhibit viral replication by lg $ID_{50}$24 2. This permits to classify RNA-M as a substance with high antiviral activity.

The study of prophylactic and therapeutic effects of RNA-M was performed on a rabbit kidney cell culture (RK13). Type 1 herpes virus (HSV, VC strain), infectious titer −4.0 lg $CCID_{50}$ and type 2 herpes virus (strain BH), infectious titer 4.0-5.0 lg $CCID_{50}$ were used. For the study of prophylactic effect of RNA-M, the drug at different concentrations was introduced 24 hours before infecting the cell culture with virus, while for the study of its the therapeutic effect RNA-M was added to the cell culture 24 hours after infecting with virus. The cultures were incubated in a thermostat with $CO_2$ supply for 5 days with daily microscopic control of viral replication as assessed by viral cytopathic action on RK13 cells compared with control cultures where the monolayer was not subject to any influences. Morphologically the cytopathic action is characterized by formation of symplasts or round-shaped cells along with giant multinuclear cells. After 5 days the medium was removed from well plates for assessment of infectious titer in each sample subject to prophylactic and therapeutic action of RNA-M. Results of HSV-1 and HSV-2 replication are presented in Table 2.3.1. below.

TABLE 2.3.1

Prophylactic and therapeutic effects of RNA-M on HSV-1 and HSV-2 in a RK13 cell culture

| Concentration, mg/ml | Infectious titer, lg $CCID_{50}$ | Inhibition, lg $CCID_{50}$ | Infectious titer, lg $CCID_{50}$ | Inhibition, lg $CCID_{50}$ |
|---|---|---|---|---|
| | Prophylactic effect, HSV-1 | | Prophylactic effect, HSV-2 | |
| 10 | 1.0 | 3.0 | 1.0 | 3.0 |
| 5 | 1.0 | 3.0 | 1.0 | 3.0 |
| 2.5 | 1.0 | 3.0 | 0 | 4.0 |
| 1.25 | 1.0 | 3.0 | 0 | 4.0 |
| 0.6 | 2.0 | 2.0 | 0 | 4.0 |
| Control | 4.0 | | 4.0 | |
| | Therapeutic effect, HSV-1 | | Therapeutic effect, HSV-2 | |
| 10 | 4.0 | 0 | 1.0 | 4.0 |
| 5 | 2.0 | 2.0 | 1.0 | 4.0 |
| 2.5 | 1.0 | 3.0 | 1.5 | 3.5 |
| 1.25 | 1.0 | 3.0 | 0 | 5.0 |
| 0.6 | 0 | 3.0 | 0 | 5.0 |
| Control | 4.0 | — | 5.0 | |

As seen from Table 2.3.1., RNA-M exhibited a high antiherpetic activity in a wide range of concentrations from 0.6 до 10 mg/ml in therapeutic as well as in prophylactic regimen of administration into a RK13 cell culture.

Mitotic characteristics in prophylactic and therapeutic regimens of administration of 0.1 and 1.0 mg/ml of RNA-M were studied on NGUK cells as shown in Table 2.3.2. below.

TABLE 2.3.2

The effect of RNA-M on mitotic regimen of HSV-infected NGUK cells

| Regimen | Treatment and infecting, mg/ml | Mitotic index, ‰ | Anomalous mitoses, % |
|---|---|---|---|
| Prophylactic | RNA-M 1.0 + HSV | 8.6 | 19.0 |
| | RNA-M 0.1 + HSV | 19.4 | 19.3 |
| | HSV | 8.7 | 35.8 |
| | Intact cells | 20.8 | 19.4 |
| Therapeutic | HSV + RNA-M 1.0 | 20.3 | 18.0 |
| | HSV + RNA-M 0.1 | 22.0 | 19.1 |
| | HSV | 6.0 | 38.3 |
| | Intact cells | 21.6 | 17.5 |
| | RNA-M 1.0 | 19.9 | 21.3 |

As seen from Table 2.3.2., prophylactic administration of 0.1 mg/ml of RNA-M prevented the changes of cellular mitotic regimen. Mitotic activity in study groups was not significantly different from that in control group (intact cells). Analysis of pathological forms of mitoses did not reveal significant differences either. Therefore, 0.1 mg/ml of RNA-M (for prophylactic purpose) and 1 mg/ml of RNA-M (for therapeutic purpose) did not adversely affect the mitotic activity index nor the count of pathological mitoses.

Example 2.3.2. In Vivo Models of Herpes Viruses

Animals. The animals used were white non-inbred mice weighting 14 to 18 g kept under standard vivarium conditions. Guinea pigs, cavies (males) weighting 250 to 300 g. The RNA-M antiherpetic action (HSV-1) was studied in a model of herpetic meningoencephalitis. Animals were infected by means intracerebral injection of 0.03 ml of viral suspension. Virus activity evaluation was based on animal lethality assessment. The used model is convenient for symptom analysis, is characterized by 100% reproducibility, and does not require additional controls. The onset of clinical symptoms was observed on the 5th to 6th day after infection and reached its maximum on the 13th to 14$^{th}$ day. Subsequently, a decrease of clinical manifestations was observed with further reconvalescence of survivor animals. The presence of acute herpetic infection was confirmed by immunofluorescence. The most intensive fluorescence was observed in the brain tissues, especially in the brain stem area. It was observed 6-7 days after infection, correlating with the onset of clinical manifestations. Lethality of animals infected with the herpes simplex virus constituted 100%.

RNA-M antiherpetic activity (HSV-2) was also studied in a model of genital herpetic infection in guinea pigs. The infection was modeled by infecting guinea pigs with a virus-containing fluid with the infectious titer of 5.0-5.5 lg CCID$_{50}$/ml according to Marennikova method. (Marennikova S. S., Matsevich G. R., Chekunova E. V. et al., The development and use of new experimental models of different forms of herpes infection, Vopr. virusol., 1986, 1, pp. 59-65) The virus-containing fluid was rubbed into previously scarified penis skin. Scarification was performed with a surgical lance under ether anesthesia. The scarification surface was 4-7 mm². The virus-containing fluid was placed with a pipette right after scarification and subsequently rubbed in. Clinical symptoms of experimental genital herpes were registered daily before initiation of treatment and followed up throughout the whole disease period. The criteria for evaluation of severity of infectious process included the surface and degree of specific lesions, the presence of edema, hyperemia, orchitis. Each characteristic was assessed on a 4 point scale (4 points were defined as maximal manifestation). Follow-up was performed on all animals for 21 days. Each study group consisted of 3 animals. RNA-M was placed on a scarified skin once daily for 5 days. The Virolex® ointment (KRKA, Slovenia) was used as a standard medication for comparison. Similarly, Virolex® was applied daily on a scarified skin for 5 days. Treatment with RNA-M or Virolex® was initiated 2 hours after infection. The antiherpetic activity of RNA-M in vivo was studied on a white non-inbred mice model of herpetic meningoencephalitis. RNA-M (0.5 and 5 mg/ml) and Virolex (10 mg/kg) were injected intraperitoneally (0.2 ml) 24 hours after infecting with herpes virus. The concentration of 0.5 mg/kg of RNA-M has been shown to have a high therapeutic efficacy, its effectiveness index resulted 41.2, i.e., it was almost equal to that of the standard medication Virolex® (effectiveness index 50.0). Antiviral activity of RNA-M was also assessed on a model of genital herpes in guinea pigs. The treatment with RNA-M was administered in dosage of 0.1 and 1.0 mg/kg before and after infecting with herpes virus. Virolex® was used as a control drug. The experiment involved 5 groups of animals: animals infected with herpes virus only; animals infected with herpes virus and treated with Virolex®; animals infected with herpes virus and treated with topical RNA-M 1.0 mg/kg; animals infected with herpes virus and treated with RNA-M 0.1 mg/kg; animals which received topical RNA-M 1.0 mg/kg and further infected with herpes virus. The results of evaluation of RNA-M efficacy on a model of genital herpes in guinea pigs are presented in Table 2.3.3. below.

TABLE 2.3.3

Efficacy of RNA-M on a model of genital herpes

| Dose, mg/kg | Duration of the disease | Mean intensity of disease manifestations | Therapeutic activity index, % | P |
|---|---|---|---|---|
| Prophylaxis | | | | |
| RNA-M 1.0 | 0 | 0 | 100 | >0.001 |
| RNA-M 0.1 | 0 | 0 | 100 | >0.001 |
| RNA-M | 5.0 | 10 | 82 | >0.001 |

TABLE 2.3.3-continued

Efficacy of RNA-M on a model of genital herpes

| Dose, mg/kg | Duration of the disease | Mean intensity of disease manifestations | Therapeutic activity index, % | P |
|---|---|---|---|---|
| Treatment | | | | |
| RNA-M 1.0 | 7 | 14 | 73.2 | >0.001 |
| RNA-M 0.1 | 5 | 14 | 73.2 | >0.001 |
| Virolex | 9.75 | 22 | 56.0 | >0.001 |
| Control | 15 | 56 | 0 | — |

In prophylactic regimen of administration of RNA-M (0.1 mg/kg and 1.0 mg/kg) the mean intensity of disease manifestations was equal to zero, and therapeutic activity index was 100%. The same indices of Virolex® action were much lower. The effect of treatment of animals with RNA-M after infection was also significantly superior to Virolex®. The mean intensity of disease manifestations was equal to 14 for RNA-M and 22 for Virolex®, while the therapeutic activity index was 73.2 and 56.0, respectively.

The results of the present study demonstrate a high antiviral activity of RNA-M in a wide range of concentrations in both prophylactic and therapeutic regimens of administration. It was found to be significantly superior to Virolex®.

2.3.3. Treatment of Herpes Virus Disease in Human Patients

A leading role in the treatment of herpes-virus disease belongs to chemotherapeutic drugs, which include abnormal nucleosides (acyclovir and its derivatives), which inhibit the synthesis of viral DNA and viral replication by competitive inhibition of viral DNA polymerase. However, these drugs are toxic, especially during prolonged using, and, in some cases, they are ineffective in accordance to development of herpes-viruses resistance.

Thus, the effectiveness of using the RNA-M in treatment of genital herpes in human patients was assessed.

Included in the study were patients who applied in connection with genital herpes.

Investigation of ½ type's herpes replication in vaginal scrapings or swabs from the urethra was performed with help of polymerase chain reaction. All patients have been registered with a high concentration of DNA copies (+++) HSV 1 or 2 type. The therapy with RNA-M has been prescribed to the patients in dosage of 0.5 gr. 3 times per day after meals. The patients with similar results of PCR but with treatment with "Placebo" were used as a control group. All patients have been examined again one month lately after starting therapy.

The polymerase chain reaction was negative in 83.3% of cases in treatment group and the presence of pathogens DNA in low concentrations (+) was only in 16.7% of the survey. 71.4% of patients with positive result at additional examination with PCR were observed in control group.

These results confirmed the effectiveness and feasibility of using the RNA-M in genitals herpes treatment.

Example 2.4. Models of HIV

Example 2.4.1. HIV Reproduction Model

Human immunodeficiency virus (reference strain BUI-1$_{RF}$) in the form of producing cell culture MT4/BIII LBK—T-human lymphocytes—producing HIV-1 virus obtained from the museum of D. Ivanovsky Institute of Virology. The virus was stored at −70° C. The source of HIV was the culture medium of MT4/BIII LBK cells. As beforehand detected by means of indirect immunofluorescence, with monoclonal antibodies to p-24 HIV antigen, the number of infected cells reached almost 100%. Neutralization reaction confirmed similarity of HIV-1 to strains produced by MT4/BIII LBK cells.

Cell culture. Lymphoblastoid MT-4 cells were obtained from cell repository of the Institute of Experimental Pathology, Oncology, and Radiobiology of the National Academy of Sciences of Ukraine. The nutrient medium consisted of 88% of the RPMI 1640 ("Sigma'") medium with 10% heat-inactivated fetal calf serum ("Sigma>) and antibiotics. The cells were grown in 50 ml plastic culture bottles ("Nunc") at 37° C. and in 5% $CO_2$. Every 3-4 days the living cells were counted with the use of trypan blue and disseminated in initial concentration of $2.5\times10^5$ cells per 1 ml.

Study of anti-HIV action of RNA-M. A standard model of primarily HIV-infected suspension MT-4 cells was used. Infecting of MT-4 cells with HIV was performed by addition of virus (100 $ID_{50}$/well) to a cell suspension containing 4-5× $10^5$ cells/ml. Inhibiting effect of drugs was assessed on the $5^{th}$ day of cultivation by quantitative evaluation of viral antigen with the use of immunoenzyme assay. HIV-1 infectious titer was assessed as follows: ten-fold dilutions of the tested medium were introduced into polystyrene well plates containing MT-4 cells. The infected cells were cultivated at 37° C. for 5 days in 5% $CO_2$ gas mixture. Thereafter, the culture fluid from each well was analyzed for the presence of p24 antigen with the use of immunoenzyme assay "Genetic Systems™ HIV-1 Ag EIA" (BioRad). HIV infectious titer was equal to 4.0-6.5 lg ID50.

Study of Specific Anti-HIV RNA-M Activity in a Cell Culture. HIV was cultivated in a suspension culture MT-4 and in a re-inoculated rat gasserian ganglion neurinoma (RGGN) cell culture. HIV-1 characteristics are presented in Table 2.4.1. below.

TABLE 2.4.1

Characteristics of human immunodeficiency virus

| Cell culture | P24 expression (OD 492) | HIV infectious titer, lg $ID_{50}$ |
|---|---|---|
| MT-4 | 3.069 | 6.0 |
| RGGN | 3.024 | 4.5 |

The study of M-RNA and RNA-A was performed on a MT-4 cell culture. (Tkachuk Z. YU., Rybalko S. L., Semernikova L. I., Tkachuk V. V., Zavelevich M. P., Tkachuk L. V., Myhaylopulo I., Matsuka H. KH., Action of 2',5'-tryolihoadenilate and its epoxy-derivative on reproduction of human immunodeficiency virus and reverse transcriptase activity of retroviruses, Biopolymers and cells, 1999, 15, 4, pp. 314-319) RNA-M was added 24 hours after infecting with virus. HIV was introduced to each sample with subsequent cultivation for 5 days. Then, infectious titer was measured in each sample. The study dnigs remained in the medium throughout the whole cycle of the study. A Retrovir® 0.25 dilution was used as a reference drug. Shown that the preparations of RNA-M and RNA-A significantly inhibited the reproduction of HIV at the 1.9 Lg ID 50 in the scheme used injection drugs. Retrovir had a similar effect. The results of the present study demonstrate a high antiviral activity of RNA-M and RNA-A at therapeutic regimens of administration. It was found to be significantly superior to Retrovir®. This permitted to conclude the RNA-M and RNA-A to be effective in inhibiting HIV reproduction.

Example 2.4.2. Treatment of AIDS in Human Patients

Tactic of conduct of patients with HIV-infection consists in regular laboratory control after the $CD4^+$ T-lymphocytes and viral loading. In that case, when the amount of CD $4^+$ T-lymphocytes becomes less than 350 cells in 1 mcl of blood and viral loading exceeds 100000 copies of HIV RNA in 1 ml of blood, antiretroviral therapy (ART) should be prescribed. The effect of application of RNA-M on the amount of CD $4^+$ T-lymphocytes and viral loading in HIV-infected persons was studied.

Three group of men with 1 and 2 clinical stage got RNA-M inward for 0.75 gr per day during 2 month. They did not get specific ART, in a kind absence of testimonies. Determination of level of CD 4+ T-lymphocytes and viral loading in 1 month and in 2 months of treatment was conducted. After the first month of application of RNA-M in this groups the viral loading was decline in 1.7, 1.9 and in 12.7 times, by comparison to primary indexes. In all three group the absolute amount of CD 4+ T-lymphocytes grew on the average on 285 cells in 1 mcl of blood (350, 351 and 154 cells/mcl). The general amount of lymphocytes grew in peripheral blood on the average on 579.67 cells in 1 mcl of blood. After the 2th month of treatment for the first group the fall-off of the viral loading from 13000 to 1190 RNA copies of HIV in 1 ml of blood (in 10.9 times). For a patient second group the viral loading of HIV was changed from 1780 to 151 RNA copies in 1 ml of blood. For the patient third group viral loading decreased 3.3 times. During the first and second month of the use of RNA-M it is not discovered in the indexes of biochemical blood test (transaminases, bilirubine, albumine, urea, kreatinine, cholesterol and others like that). Application RNA-M in the dose of 0.75 mg per day for the HIV-infected persons results in the decline of level of the viral loading of HIV and increase amount of $CD4^+$ T-lymphocytes.

Example 2.5. Models of Enteroviral Infection

A Hep-2 cell culture is a re-inoculated human laryngeal carcinoma cell culture. Nutrient medium—Igla MEM+10% embryonic serum at 37° C.+5% $CO_2$. Virus—Coxsackie B virus, infectious titer 4 $lgEID_{50}$. Maximum tolerance concentration (MTC), or $CD_{50}$ of RNA-M and RNA-A was 5 mg/ml. Maximum tolerance concentration (MTC) was defined as the maximum concentration of the drug which was decreasing the number of living cells by 50%. The chemotherapeutic index (CTI) of RNA-M and RNA-A with regard to Coxsackie B virus was calculated as the ratio of the MTC to the minimum active concentration (MAC). MAC was defined as the lowest concentration of the drug capable of inhibiting the virus-specific cytopathic action by 50%. For MAC evaluation the test-virus infecting dose was introduced into Hep-2 cell culture and incubated at 37° C. for 1 hour in a gas mixture containing 5% $CO_2$. After viral adsorption on the cells, it was removed and the cells were washed three times with Hanks' solution (0.4 ml per each well). Thereafter, 0.2 ml of maintenance medium with different concentrations of the study drugs was introduced into each well. Three wells were used per each drug concentration. Infected cells incubated in the maintenance medium were used as control. The cells were incubated for 48 hours at 37° C. in a gas mixture containing 5% $CO_2$. The absence of cytopathic action in study wells while it was absent in control wells permitted to establish the drug MAC. The drug is considered to possess antiviral properties if it is capable to decrease the viral reproduction by 2.0 lg or more. Thus, the MAC of RNA-A was estimated to be >500 mcg/ml, and MAC of RNA-M appeared to be 125 mcg/ml. Evaluation of chemotherapeutic index of both drugs with regard to Coxsackie B virus showed that for RNA-M its value was 40, while for RNA-A it was equal to 10. Hence MTC, MAC, and chemotherapeutic index of both drugs permits to classify RNA-M as an active antiviral agent, while RNA-A belongs to drugs with low anti-enteroviral activity.

The invention claimed is:

1. A method of preparing a composition for preventing or treating an infection by a virus, comprising heating a purified yeast RNA extract with mannitol to a temperature in the range 40-70° C., so as to obtain a composition comprising the purified RNA extract combined with mannitol, wherein the yeast RNA extract comprises nucleotide fragments having 25±10 nucleotides with a purity degree of at least 99% by weight, wherein the yeast RNA extract and mannitol are present in the composition in a proportion of from about 2:1 to about 3:1 by weight, and wherein the RNA extract constitutes at least about 50% by weight of the composition.

2. The method of claim 1, comprising processing the RNA extract with alkaline amino acids.

3. The method of claim 1, comprising processing the RNA extract with arginine.

4. The method of claim 1, wherein the yeast is Sacchsromyces cerevisiae.

5. The method of claim 1, wherein the yeast is Candida utilis.

6. The method of claim 1, wherein the purified RNA extract is substantially free of proteins, DNA, and nucleotides.

7. The method of claim 1, wherein the purified RNA is a yeast extract containing more than 14.5% by weight of nitrogen and more than 8.5% by weight of phosphorus.

8. The method of claim 1, wherein the composition comprises the purified RNA extract combined with the mannitol in an amount effective to prevent or treat an infection by a virus in a patient.

9. The method of claim 8, wherein the composition comprises an amount of purified yeast RNA capable of inhibiting virus reproduction.

10. The method of claim 8, wherein the composition comprises an amount of purified yeast RNA effective to inhibit receptors of the virus which provide for virus replication in cells.

11. The method of claim 8, wherein the virus is selected from Orthomyxoviridae family.

12. The method of claim 11, wherein the virus is an anthroponosis acute respiratory virus.

13. The method of claim 8, wherein the virus is selected from Paramyxovirus family.

14. The method of claim 8, wherein the virus is of Hepatitis kind.

15. The method of claim 14, wherein the virus is Hepatitis C virus.

16. The method of claim 8, wherein the virus is selected from Herpesviridae family.

17. The method of claim 8, wherein the virus is selected from herpes simplex virus.

18. The method of claim 8, wherein the virus is genital herpes virus.

19. The method of claim 8, wherein the virus is influenza virus.

20. The method of claim 19, wherein the virus is influenza virus of H1N1 strain.

21. The method of claim 19, wherein the virus is influenza virus of H5N2 strain.

22. The method of claim 8, wherein the virus is a human immunodeficiency virus.

23. The method of claim 8, wherein the virus is an enterovirus.

24. The method of claim 23, wherein the virus is a Coxsackie B virus.

25. The method of claim 8, wherein the virus is an adenovirus.

26. The method of claim 1, wherein the composition is in a form suitable to be administered intra-nasally, subcutaneously, per-orally, intra-abdominally, intra-muscularly, intra-venously, or locally at an area of virus infection or nidus of infection.

27. The method of claim 1, wherein the composition is in a form suitable to be administered in the form of an injection, capsule, pill, suppository, gel, or spray.

* * * * *